United States Patent
Winkelman et al.

(10) Patent No.: US 9,017,610 B2
(45) Date of Patent: *Apr. 28, 2015

(54) METHOD OF DETERMINING A COMPLETE BLOOD COUNT AND A WHITE BLOOD CELL DIFFERENTIAL COUNT

(75) Inventors: James Winkelman, Chestnut Hill, MA (US); Milenko Tanasijevic, West Newton, MA (US); David Zahniser, Wellesley, MA (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 364 days.

This patent is subject to a terminal disclaimer.

(21) Appl. No.: 12/430,885

(22) Filed: Apr. 27, 2009

(65) Prior Publication Data
US 2009/0269799 A1    Oct. 29, 2009

Related U.S. Application Data

(60) Provisional application No. 61/047,920, filed on Apr. 25, 2008.

(51) Int. Cl.
*G01N 1/28* (2006.01)
*G01N 1/31* (2006.01)
*G01N 1/30* (2006.01)
*C12M 1/34* (2006.01)
*G01N 35/00* (2006.01)
*G01N 15/14* (2006.01)

(52) U.S. Cl.
CPC ........ *G01N 1/2813* (2013.01); *G01N 35/00029* (2013.01); *G01N 1/312* (2013.01); *G01N 15/1475* (2013.01)

(58) Field of Classification Search
CPC .. G01N 15/1475; G01N 1/2813; G01N 1/312
See application file for complete search history.

(56) References Cited

U.S. PATENT DOCUMENTS

| | | |
|---|---|---|
| 3,503,684 A | 3/1970 | Preston, Jr. et al. |
| 3,572,890 A | 3/1971 | Adamik |
| 3,888,206 A | 6/1975 | Faulkner |
| 3,960,488 A | 6/1976 | Giaever |
| 3,985,096 A | 10/1976 | Guimbretiere |

(Continued)

FOREIGN PATENT DOCUMENTS

| | | |
|---|---|---|
| CN | 1385701 | 12/2002 |
| CN | 1793919 | 6/2006 |

(Continued)

OTHER PUBLICATIONS

M. Joan Dunlop et al., "Kinetics of Adhesive Interaction In-Vitro of Human Erythrocytes in Plasma," Microvascular Research, 28(1): 62-74 (1984).

(Continued)

*Primary Examiner* — P. Kathryn Wright
(74) *Attorney, Agent, or Firm* — Fish & Richardson P.C.

(57) ABSTRACT

Systems and methods analyzing body fluids such as blood and bone marrow are disclosed. The systems and methods may utilize an improved technique for applying a monolayer of cells to a slide to generate a substantially uniform distribution of cells on the slide. Additionally aspects of the invention also relate to systems and methods for utilizing multi color microscopy for improving the quality of images captured by a light receiving device.

30 Claims, 11 Drawing Sheets

(56) References Cited

U.S. PATENT DOCUMENTS

| | | |
|---|---|---|
| 4,094,196 A | 6/1978 | Friswell |
| 4,175,859 A | 11/1979 | Hashizume et al. |
| 4,207,554 A | 6/1980 | Resnick et al. |
| 4,285,907 A | 8/1981 | Hugemann et al. |
| 4,362,386 A | 12/1982 | Matsushita et al. |
| 4,395,493 A | 7/1983 | Zahniser et al. |
| 4,465,212 A | 8/1984 | Boone |
| 4,468,410 A | 8/1984 | Zeya |
| 4,478,095 A | 10/1984 | Bradley et al. |
| 5,123,055 A | 6/1992 | Kasdan |
| 5,209,903 A | 5/1993 | Kanamori et al. |
| 5,338,688 A | 8/1994 | Deeg et al. |
| 5,419,279 A | 5/1995 | Carrico, Jr. et al. |
| 5,436,978 A | 7/1995 | Kasdan |
| 5,625,705 A | 4/1997 | Recht |
| 5,650,332 A | 7/1997 | Gao et al. |
| 5,658,802 A | 8/1997 | Hayes et al. |
| 5,665,309 A | 9/1997 | Champseix |
| 5,665,312 A | 9/1997 | Sperber et al. |
| 5,676,910 A | 10/1997 | Levine et al. |
| 5,738,728 A | 4/1998 | Tisone |
| 5,741,554 A | 4/1998 | Tisone |
| 5,743,960 A | 4/1998 | Tisone |
| 5,766,549 A | 6/1998 | Gao et al. |
| 5,804,145 A | 9/1998 | Gao et al. |
| 5,807,522 A | 9/1998 | Brown et al. |
| 5,882,933 A | 3/1999 | Li et al. |
| 6,110,425 A | 8/2000 | Gao et al. |
| 6,132,353 A | 10/2000 | Winkelman et al. |
| 6,150,173 A | 11/2000 | Schubert |
| 6,151,405 A | 11/2000 | Douglass et al. |
| 6,228,652 B1 | 5/2001 | Rodriguez et al. |
| 6,249,344 B1 | 6/2001 | Virag |
| 6,258,322 B1 | 7/2001 | Meikle |
| 6,268,611 B1 | 7/2001 | Pettersson et al. |
| 6,269,846 B1 | 8/2001 | Overbeck et al. |
| 6,287,791 B1 | 9/2001 | Terstappen et al. |
| 6,319,470 B1 | 11/2001 | Lefevre et al. |
| 6,350,613 B1 | 2/2002 | Wardlaw et al. |
| 6,398,705 B1 | 6/2002 | Grumberg et al. |
| 6,489,625 B1 | 12/2002 | Takahashi et al. |
| 6,519,355 B2 | 2/2003 | Nelson |
| 6,553,135 B1 | 4/2003 | Douglass et al. |
| 6,576,295 B2 | 6/2003 | Tisone |
| 6,590,612 B1 | 7/2003 | Rosenqvist |
| 6,711,283 B1* | 3/2004 | Soenksen ............... 382/133 |
| 6,718,053 B1 | 4/2004 | Ellis |
| 6,869,570 B2 | 3/2005 | Wardlaw |
| 6,902,703 B2 | 6/2005 | Marquiss |
| 7,006,674 B1 | 2/2006 | Zahniser et al. |
| 7,025,933 B2 | 4/2006 | Ganz et al. |
| 7,105,081 B2 | 9/2006 | Gascoyne et al. |
| 7,105,295 B2 | 9/2006 | Bass et al. |
| 7,109,477 B2 | 9/2006 | Kuzan et al. |
| 7,190,818 B2 | 3/2007 | Ellis |
| 7,297,311 B2 | 11/2007 | Tamura et al. |
| 7,300,804 B2 | 11/2007 | Sellek-Prince |
| 7,327,901 B2 | 2/2008 | Karlsson et al. |
| 7,368,080 B2 | 5/2008 | Tamura et al. |
| 7,561,329 B2 | 7/2009 | Zahniser et al. |
| 7,587,078 B2 | 9/2009 | Zahniser et al. |
| 7,597,845 B2 | 10/2009 | Domack |
| 7,608,220 B2 | 10/2009 | Jin et al. |
| 7,689,038 B2 | 3/2010 | Zahniser |
| 7,716,303 B2 | 5/2010 | Moricz |
| 7,767,147 B2 | 8/2010 | Adachi et al. |
| 7,790,107 B2 | 9/2010 | Nakaya |
| 7,796,797 B2 | 9/2010 | Nakaya et al. |
| 7,820,381 B2 | 10/2010 | Lemme et al. |
| 7,833,485 B2 | 11/2010 | Higuchi et al. |
| 7,881,532 B2 | 2/2011 | Zahniser |
| 7,903,241 B2 | 3/2011 | Wardlaw |
| 7,929,121 B2* | 4/2011 | Wardlaw et al. ............. 356/39 |
| 7,929,122 B2 | 4/2011 | Wardlaw |
| 8,058,010 B2 | 11/2011 | Erickson |
| 8,081,303 B2 | 12/2011 | Levine |
| 8,263,414 B2 | 9/2012 | Pugia |
| 8,284,384 B2 | 10/2012 | Levine |
| 8,361,799 B2 | 1/2013 | Levine |
| 2002/0049391 A1 | 4/2002 | Kuracina |
| 2002/0085744 A1 | 7/2002 | Domanik et al. |
| 2002/0086431 A1 | 7/2002 | Markham et al. |
| 2002/0159919 A1 | 10/2002 | Churchill |
| 2002/0182623 A1 | 12/2002 | Lefevre |
| 2003/0030783 A1 | 2/2003 | Roche |
| 2004/0131758 A1 | 7/2004 | Jung et al. |
| 2004/0175832 A1* | 9/2004 | Hui et al. ................. 436/8 |
| 2005/0003458 A1* | 1/2005 | Moore et al. .............. 435/7.2 |
| 2005/0003464 A1 | 1/2005 | Tibbe et al. |
| 2005/0025672 A1 | 2/2005 | Nakaya et al. |
| 2005/0058330 A1 | 3/2005 | Mitsuhashi et al. |
| 2005/0074361 A1 | 4/2005 | Tanoshima et al. |
| 2005/0212837 A1 | 9/2005 | Nakagawa et al. |
| 2006/0051241 A1 | 3/2006 | Higuchi et al. |
| 2006/0144331 A1 | 7/2006 | Hanafusa et al. |
| 2006/0223172 A1* | 10/2006 | Bedingham et al. ....... 435/288.7 |
| 2006/0263902 A1 | 11/2006 | Pugia |
| 2007/0076983 A1 | 4/2007 | Doerrer |
| 2007/0128073 A1 | 6/2007 | Tappen |
| 2007/0148046 A1 | 6/2007 | Nakaya |
| 2008/0020128 A1 | 1/2008 | Van Ryper et al. |
| 2008/0210894 A1 | 9/2008 | Ahn et al. |
| 2008/0318305 A1* | 12/2008 | Angros ................... 435/283.1 |
| 2009/0032583 A1 | 2/2009 | Lapstun et al. |
| 2009/0069639 A1 | 3/2009 | Linssen et al. |
| 2009/0155841 A1 | 6/2009 | Yamasaki |
| 2009/0162862 A1 | 6/2009 | Merz |
| 2009/0176316 A1 | 7/2009 | Giter et al. |
| 2009/0191585 A1 | 7/2009 | Yamada et al. |
| 2009/0233331 A1 | 9/2009 | Ostgaard et al. |
| 2009/0269799 A1 | 10/2009 | Winkelman et al. |
| 2009/0275076 A1 | 11/2009 | Knesel et al. |
| 2010/0027868 A1 | 2/2010 | Kosaka et al. |
| 2010/0054575 A1 | 3/2010 | Zhou et al. |
| 2010/0111399 A1 | 5/2010 | Ramirez |
| 2010/0284602 A1 | 11/2010 | Winkelman et al. |
| 2011/0014645 A1 | 1/2011 | Winkelman |
| 2012/0147357 A1 | 6/2012 | Wardlaw |
| 2013/0070077 A1 | 3/2013 | Winkelman |

FOREIGN PATENT DOCUMENTS

| | | |
|---|---|---|
| CN | 1945326 | 4/2007 |
| DE | 3 503 475 | 8/1985 |
| EP | 0 810 428 | 12/1997 |
| EP | 0 861 431 | 3/2000 |
| EP | 1387171 A1 | 2/2004 |
| EP | 1804046 A2 | 7/2007 |
| EP | 1 812 799 | 8/2007 |
| EP | 1 957 205 | 8/2008 |
| EP | 2 072 993 | 6/2009 |
| EP | 2083375 A1 | 7/2009 |
| EP | 2 202 523 | 6/2010 |
| GB | 1349379 | 4/1974 |
| JP | 60-162955 | 8/1985 |
| JP | 07-020650 | 1/1995 |
| JP | 7-83817 | 3/1995 |
| JP | 2008-507806 | 8/1996 |
| JP | 2009-033411 | 2/1997 |
| JP | 11-326208 | 11/1999 |
| JP | 2005-00573 | 1/2000 |
| JP | 2001-174456 | 6/2001 |
| JP | 2001-518186 | 10/2001 |
| JP | 2002-516982 | 6/2002 |
| JP | 2005-000573 A | 1/2005 |
| WO | 94/20856 | 9/1994 |
| WO | WO9718457 A1 | 5/1997 |
| WO | WO 97/26541 | 7/1997 |
| WO | WO 99/44593 | 9/1999 |
| WO | WO9963324 | 12/1999 |
| WO | WO 01/04276 | 1/2001 |
| WO | WO 2005/022125 | 3/2005 |
| WO | WO 2005/080940 | 9/2005 |
| WO | WO 2006/024716 | 3/2006 |

(56) References Cited

FOREIGN PATENT DOCUMENTS

| WO | WO2007067847 A2 | 6/2006 |
|---|---|---|
| WO | WO2006127631 A1 | 11/2006 |
| WO | WO 2007/105198 | 9/2007 |
| WO | WO 2008/046292 | 4/2008 |
| WO | WO 2008/140969 | * 11/2008 |
| WO | WO 2009/033128 | 3/2009 |
| WO | WO 2010/053869 | 5/2010 |

OTHER PUBLICATIONS

H. M. Aus et al., "Bone Marrow Cell Scene Segmentation by Computer-Aided Color Cytophotometry," The Journal of Histochemistry and Cytochemistry, vol. 25, No. 7, pp. 662-667 (1977).

James E. Green, "A Practical Application of Computer Pattern Recognition Research the Abbott ADC-500 Differential Classifier," The Journal of Histochemistry and Cytochemistry, vol. 27, No. 1, pp. 160-173 (1979).

John F. Brenner et al., "An Automated Microscope for Cytologic Research a Preliminary Evaluation," The Journal of Histochemistry and Cytochemistry, vol. 24, No. 1, pp. 100-111 (1976).

Aller, R., et al., "High Volume Hematology Analyzers: Getting Better All the Time", CAP Today, pp. 27-34 (Dec. 2000).

Bacus, J., "Erythrocyte Morphology and Centrifugal 'Spinner' Blood Film Preparations", The Journal of Histochemistry and Cytochemistry, vol. 22:506-516 (1974).

Bacus, J.W., "Quantitative Morphological Analysis of Red Blood Cells", Blood Cells, vol. 6:295-314 (1980).

Bacus, J.W., "Cytometric approaches to red blood cells", Pure & Appl. Chem., vol. 57:593-598 (1985).

Bacus, J.W., "Digital Image Processing Measurements of Red Blood Cell Size and Hemoglobin Content", Advances in Hematological Methods: The Blood Count, Chapter 14, 158-181 (1982).

Brenner, J.F., et al., "Automated Classification of Normal and Abnormal Leukocytes", The Journal of Histochemistry and Cytochemistry, vol. 22:697-706 (1974).

Brochure—Iris Diagnostics Case Study: New Automated Urinalysis Workcell Review.

Daoust, P.R., "The Clinical Detection of Variations in the Concentrations of Noral Leukocyte Types: A Laboratory Comparison of 100-Cell Manual Differential Counts on Wedge Smears and 500-Cell Counts by the ADC500", Blood Cells, vol. 6:489-496 (1980).

Kingsley, T.C., "The Automated Differential; Pattern Recognition Systems, Precision, and the Spun Smear", Blood Cells, vol. 6:483-487 (1980).

Lehman, C., et al., "Image Technology and its Role in Hematology", Advance/Laboratory, pp. 84-88 (May 2000).

Meyer, E., "Vickers Continuous Film", Cytology Automation: Proceedings of Second Tenovus Symposium, Cardiff $24^{th}$-$25^{th}$, pp. 147-153 (Oct. 1968).

Miller, M.N., "Design and Clinical Results of Hematrak®: An Automated Differential Counter", IEEE Transactions on Biomedical Engineering, vol. BME-23:400-405 (1976).

Novis, D., et al., "Laboratory Productivity and the Rate of Manual Peripheral Blood Smear Review: A College of American Pathologists Q-Probes Study of 95141 Complete Blood Count Determinations Performed in 263 Institutions", Archives of Pathology and Laboratory Medicine, vol. 130:596-601 (2006).

Promotional materials for DRD™ Diluter Corporation's Little Squirt™, NanoBlast-96™, and Differential NanoPipettor™/Diluter.

Rogers, C., "Blood Sample Preparation for Automated Differential Systems", American Journal of Medical Technology, vol. 39: 435-442 (1973).

Seiter, C., et al., "Contact Angles: New Methods and Measurements", American Laboratory, p. 26 (Feb. 2002).

Smit, J.W., et al., "A commercially available interactive pattern recognition system for the characterization of blood cells: description of the system, extraction and evaluation of simple geometrical parameters of normal white cells", Clin. Lab. Haemat. vol. 1:109-119 (1979).

Walker, T., "Comparative Evaluation of the Iris iQ200 Body Fluid Module with Manual Hemacytometer Count", American Journal of Clinical Pathology, vol. 131:333-338 (2009).

Walters, J., et al., "Performance Evaluation of the Sysmex XE-2100 Hematology Analyzer", Laboratory Hematology, vol. 6:83-92 (2000).

Ward, P., "The CBC at the Turn of the Millenium: An Overview", Clinical Chemistry, vol. 46:1215-1220 (2000).

Zahniser, D.J., et al., "Detecting Infection-Related Changes in Peripheral Blood Smears with Image Analysis Techniques", Reprinted from Analytical and Quantitative Cytology, vol. 5:269-274 (1983).

Zahniser, D.J., et al., "Spectral Bandwidth in Automated Leukocyte Classification", Cytometry, vol. 7:518-521 (1986).

Paredes Sanchez, Luis-Miguel, "Notification of Transmittal of the International Search Report and the Written Opinion of the International Searching Authority, or the Declaration", International Application No. PCT/US2009/041858, issued on Aug. 10, 2010 (14 pages).

Salaün, Marion, "Notification of Transmittal of the International Search Report and the Written Opinion of the International Searching Authority, or the Declaration", Internatinal Application No. PCT/US2011/021546, issued on Jan. 18, 2011 (14 pages).

Bai, Lingfei, "Notification Concerning Transmittal of International Preliminary Report on Patentability", International Application No. PCT/US2010/032612, issued on Nov. 1, 2011 (2 pages).

Young, Lee W., "Written Opinion of the International Searching Authority", International Application No. PCT/US2010/032612, issued on Jun. 28, 2010 (11 pages).

Bacus, "An Automated Method of Differential Red Blood Cell Classification with Application to the Diagnosis of Anemia" The Journal of Histochemistry and Cytochemistry 25: 614-632 (1977).

Bacus, "Image Processing for Automated Erythrocyte Classification" The Journal of Histochemistry and Cytochemistry 24: 195-201 (1976).

Cornet et al., "Performance evaluation and relevance of the cellavision DM96 system in routine analysis and in patients with malignant hematological diseases," International Journal of Laboratory Hematology, vol. 30 pp. 536-542 (2007).

De Cresce et al., "PAPNET™ Cytological Screening System," Laboratory Medicine 22(4):276-280, Apr. 1991.

Gelemsa et al., Procedures for the automation of the white blood cell differential count; NTG/GI Gesellschaft fur Informatik Nachwichtentechnische Gesellschaft Fachtagung "Cognitive Verfahren und Systeme", Springer-Verlag, Berlin pp. 237-256 (1973).

Gulati et al., "Criteria for blood smear review," Laboratory Medicine, vol. 33, No. 5 pp. 374-377 (2002).

English translation of the Written Opinion of the International Searching Authority for PCT/CN2007/002665 dated Nov. 15, 2007, 5 pages.

International Preliminary Report on Patentability for PCT/US2009/041858, issued Feb. 28, 2012, 6 pages.

International Preliminary Report on Patentability for PCT/US2011/021546 mailed Aug. 1, 2013, 7 pages.

International Search Report and Written Opinion for PCT/US2009/041858, dated Jun. 28, 2010, 13 pages.

Office Action in U.S. Appl. No. 12/768,633 mailed Jun. 26, 2013, 15 pages.

Office Action in U.S. Appl. No. 12/768,633, dated Oct. 18, 2012, 21 pages.

Office Action in U.S. Appl. No. 12/785,314 mailed Apr. 30, 2013, 18 pages.

Office Action in U.S. Appl. No. 12/785,314 mailed Nov. 26, 2013, 41 pages.

Office Action in U.S. Appl. No. 12/785,314, dated Oct. 12, 2012, 30 pages.

Office Action in U.S. Appl. No. 12/785,337 mailed Nov. 21, 2013, 24 pages.

Office Action in U.S. Appl. No. 13/619,381, mailed Jan. 15, 2014, 7 pages.

Office Action in U.S. Appl. No. 13/619,381, mailed May 9, 2013, 16 pages.

(56) References Cited

OTHER PUBLICATIONS

Brochure—Iris Diagnostics Case Study: New Automated Urinalysis Workcell Review (2009).
Promotional materials for DRD™ Diluter Corporation's Little Squirt™ (Jan. 7, 2008).
Promotional materials for NanoBlast-96TM (Feb. 28, 2006).
Promotional materials for Differential NanoPipettorTM/Diluter, small volume sampling (Feb. 28, 2006).
Promotional materials for Differential NanoPipettorTM/Diluter (Apr. 9, 2005).
Bacus, "Quantitative Red Cell Morphology," Monogr. Clin. Cytol. 9: 1-27 (1984).
Office action mailed Sep. 10, 2013 in counterpart Japanese Application No. 2011-516238, 4 pgs.
Office action mailed Sep. 24, 2014 in counterpart Japanese Application No. 2011-516238, 3 pgs.
Examination Report mailed Aug. 21, 2014 in counterpart Australian Application No. 2009352216, 3 pgs.
Office action mailed Mar. 20, 2012 in counterpart European Application No. 09827031.7, 11 pgs.
Response to office action mailed Sep. 18, 2012 in counterpart European Application No. 09827031.7, 25 pgs.
International Preliminary Report on Patentability mailed Feb. 28, 2012 in International Application No. PCT/US2009/041858, 6 pgs.
Office Action mailed Sep. 25, 2014 in related U.S. Appl. No. 12/768,633, 20 pgs.

\* cited by examiner

Fig. 3
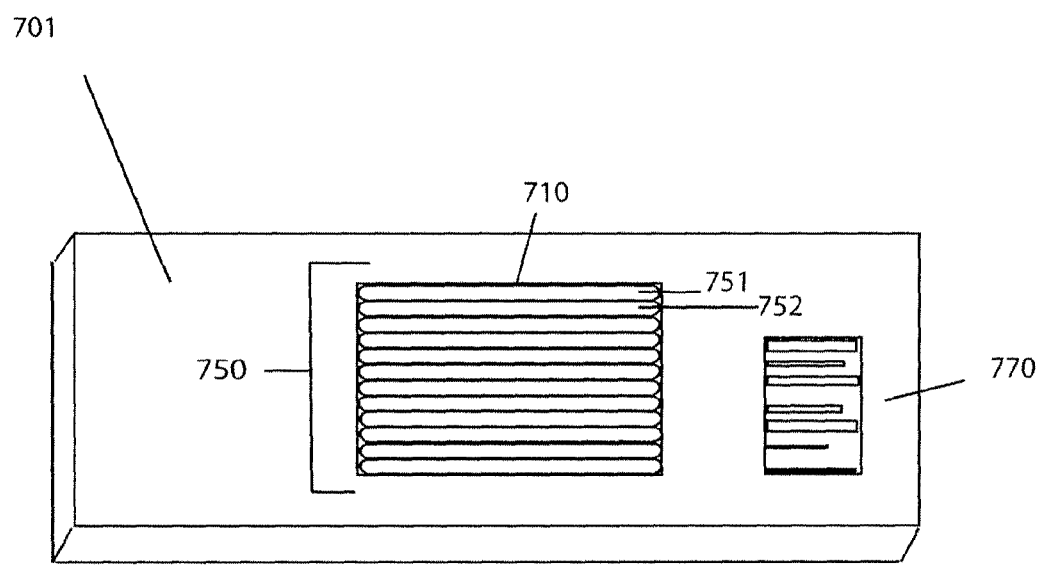
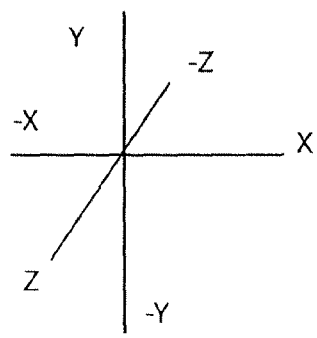

Fig. 4
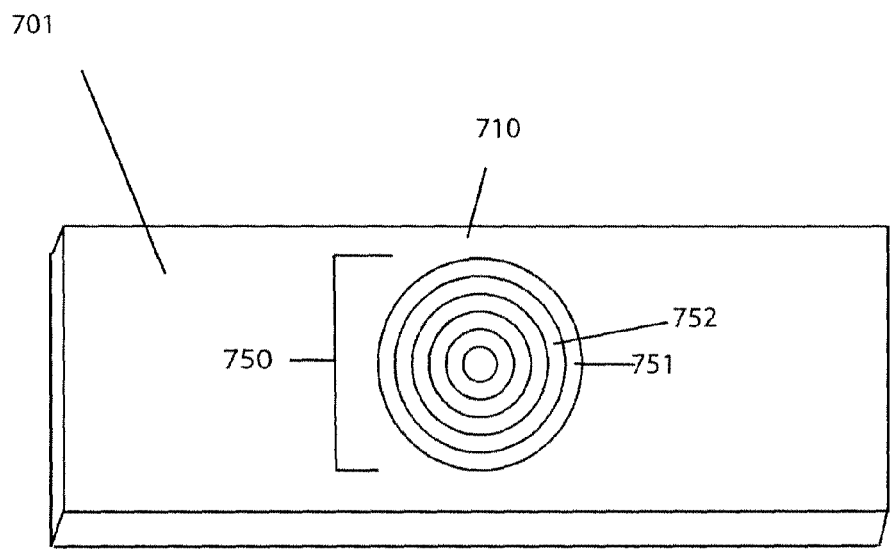
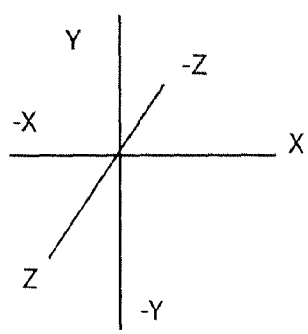

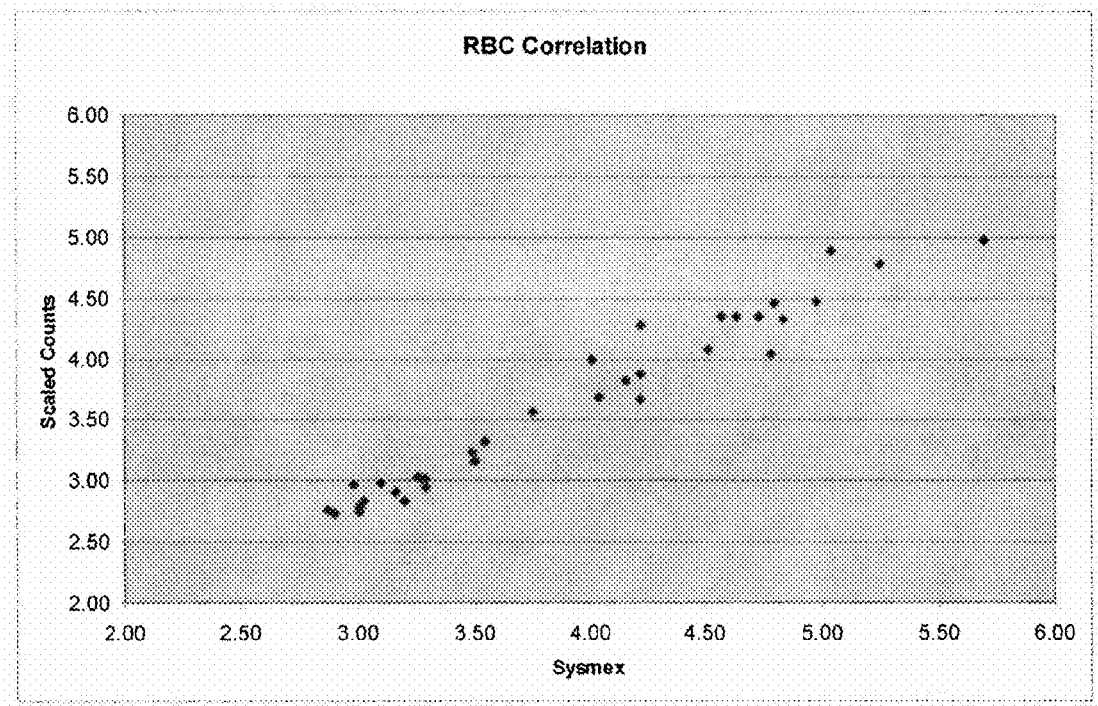

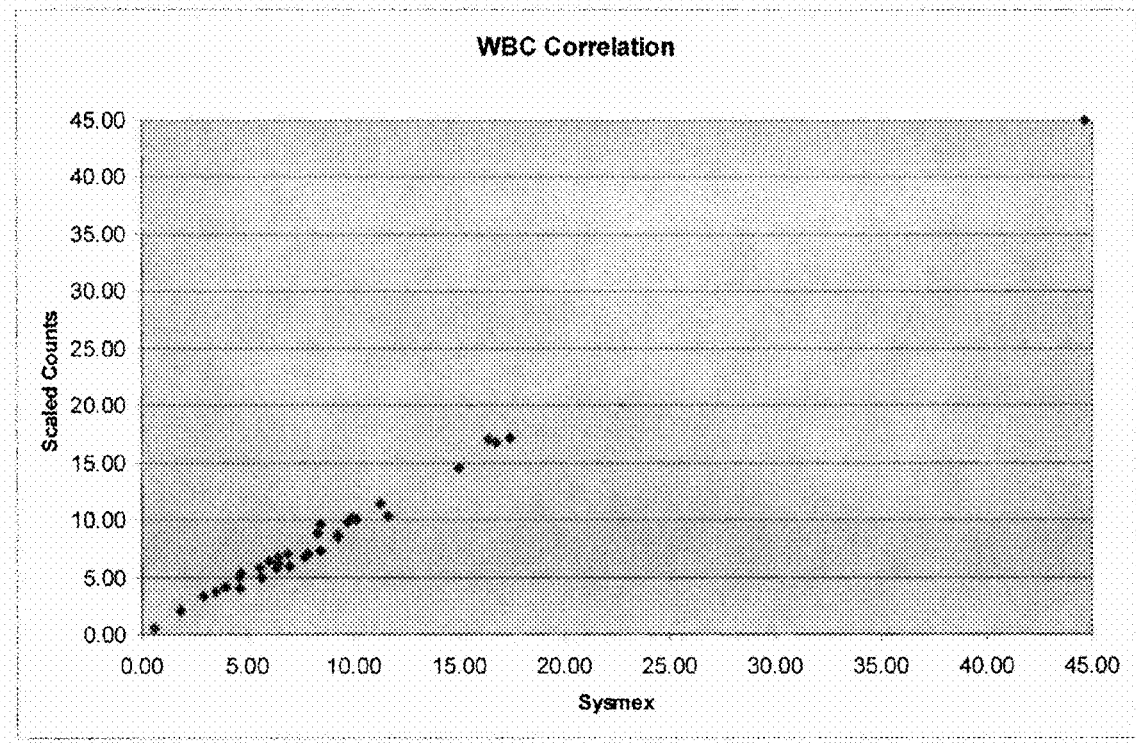

METHOD OF DETERMINING A COMPLETE BLOOD COUNT AND A WHITE BLOOD CELL DIFFERENTIAL COUNT

CROSS-REFERENCE TO RELATED APPLICATIONS

This application claims priority under 35 U.S.C. §119 to U.S. Provisional Application No. 61/047,920, filed Apr. 25, 2008, which is expressly incorporated herein by reference in its entirety. Further, the present application expressly incorporates herein by reference the application entitled "SYSTEMS AND METHODS FOR ANALYZING BODY FLUIDS," which is being filed on the same date and by the same inventors as the present application.

STATEMENT AS TO FEDERALLY SPONSORED RESEARCH

This invention was made with Government support under NIH Grant Number HL077033. The Government has certain rights in this invention.

FIELD OF THE INVENTION

This invention relates to a system and process for determining composition and components of fluids. More specifically the present invention provides improved techniques for viewing cellular morphology, and determining the number of a particular type of cell in a portion of a body fluid.

BACKGROUND OF THE INVENTION

Pathology is a field of medicine where medical professionals determine the presence, or absence of disease by methods that include the morphologic examination of individual cells that have been collected, fixed or air-dried, and then visualized by a stain that highlights features of both the nucleus and the cytoplasm. The collection of the cells often involves capturing a portion of a person's body fluid, placing the body fluid on a slide, and viewing the fluid on the slide using a microscope.

One of the most commonly performed pathologic studies is the CBC (the Complete Blood Count). To perform a CBC, a sample of blood is extracted from a patient and then the cells are counted by automated or manual methods. The CBC is commonly performed by using an instrument, based on the principal of flow cytometry, which customarily aspirates anti-coagulated whole blood and divides it into several analysis streams. Using the flow cytometer a number of primary and derived measurements can be determined including: i) red blood cell (RBC) count, hemoglobin (Hb), hematocrit (Hct), red blood cell indices (mean corpuscular volume, MCV, mean corpuscular hemoglobin, MCH and mean corpuscular hemoglobin concentration MCHC), red blood cell distribution width, enumeration of other red blood cells including reticulocytes and nucleated red blood cells, and red blood cell morphology; ii) white blood cell (WBC) count and WBC "differential" count (enumeration of the different normal white blood cell types, including neutrophils, lymphocytes, eosinophils, basophils and monocytes, and the probable presence of other normal and abnormal types of WBC that are present in various disease conditions); and iii) platelet count, platelet distribution widths and other features of platelets including morphological features. In flow cytometers, red blood cell, WBC, and platelet morphological characterizations are typically made indirectly, based on light absorption and light scattering techniques and/or cytochemically based measurements. Some advanced flow cytometers calculate secondary and tertiary measurements from the primary measurements.

Flow based CBC instruments generally require extensive calibration and control, maintenance, and skilled operators, and they have substantial costs associated with acquisition, service, reagents, consumables and disposables. One significant problem with these systems in routine use is that a large proportion of blood specimens require further testing to complete the assessment of the morphologic components of the CBC. This involves placing a sample of blood on a slide, smearing the sample against the slide to form a wedge smear, and placing the slide under a microscope. This process is often done manually by skilled medical technologists, which increases the cost and time to receive results from the tests. The direct visualization of blood cells on a glass slide must be performed whenever the results of the automated test require further examination of the blood sample. For example, a "manual" differential count is performed by direct visualization of the cells by an experienced observer whenever nucleated immature RBCs are found or WBCs suspicious for infection, leukemias or other hematologic diseases are found.

The proportion of these specimens requiring further review generally ranges from 10% to 50%, depending on the laboratory policy, patient population and "flagging" criteria, with a median rate of around 27%. The most frequent reasons for retesting include the presence of increased or decreased number of WBCs, RBCs or platelets, abnormal cell types or cell morphology, clinical or other suspicion of viral or bacterial infections.

In addition to additional work involved in performing manual differential counts, this process has a number of additional technical limitations. These include distortions of cell morphology because of mechanical forces involved in smearing the cells onto the slide, and cells overlapping one another, which makes visualization of individual cell morphology difficult.

SUMMARY OF THE INVENTION

The present invention provides systems and methods for placing cells on a slide. Additionally systems and method for imaging the cells are provided. The images may be later used to perform tests such as a complete blood count including image-based counting and assessment of the morphology of the formed elements of blood, including RBCs, WBCs, and platelets. Embodiments of the present invention may improve the accuracy of the CBC by providing improved visualization of the formed elements of blood. Aspects of the present invention may analyze and determine the presence of certain cell types, such as abnormal or immature WBCs that are found in cases of abnormal bone marrow function including hematological malignancies. Further, the configurations of the present invention may decrease costs associated with instrumentation, decrease costs of consumables and reagents, require less operator time and reagents, fewer repeated tests, and fewer moving parts than other prior art techniques. Configurations of the present invention may also reduce the turn around time for many of the CBC tests that currently require visualization of blood cells after the instrumental portion of the test is completed, by allowing cells to be visualized on a monitor instead of under a microscope.

Aspects of the present invention are effective at preserving cell morphology. This may be important for patients with hematological malignancies such as chronic lymphocytic leukemia (CLL) or acute myeloid leukemia (AML). The systems and methods relating to applying a monolayer of cells to a slide may enable detection of a larger number of morphologically well-preserved blast cells and other immature or fragile cells. This would allow their more accurate recognition at an earlier stage of the leukemic or other disease process. Certain aspects of the present invention provide for preparing a substantially uniform distribution of cells across a test area of a slide.

Aspects of the present invention also relate to collecting cells in a fluid (such as blood) from organic tissue, possibly mixing the cells contained in the fluid with a diluent, collecting a sub-sample (aliquot) of a known volume from the solution, and then depositing the aliquot onto a substratum such as a slide using a dispensing device or applicator. The cells may be allowed to air dry or may be fixed (using a fixative solution) or both, depending on the examination that is anticipated. The cells may also be stained. The stained cells on the substratum may be counted and examined by an automated imaging system utilizing a computer or viewed by manual microscopic examination. Digital images may be shown on a computer display to reduce the need for manual microscopic review.

BRIEF DESCRIPTION OF THE DRAWINGS

FIG. 3: is an enlarged top view of the slide and slide specimen.

FIG. 4: is alternate embodiment of the top view of the slide and slide specimen.

FIG. 5: is a graph illustrating the correlation between Sysmex RBC counts and the RBC counts generated using an embodiment of the instant invention.

FIG. 6: is a graph illustrating the correlation between Sysmex WBC counts and the WBC counts generated using an embodiment of the instant invention.

DETAILED DESCRIPTION OF THE INVENTION

Figure 1A:
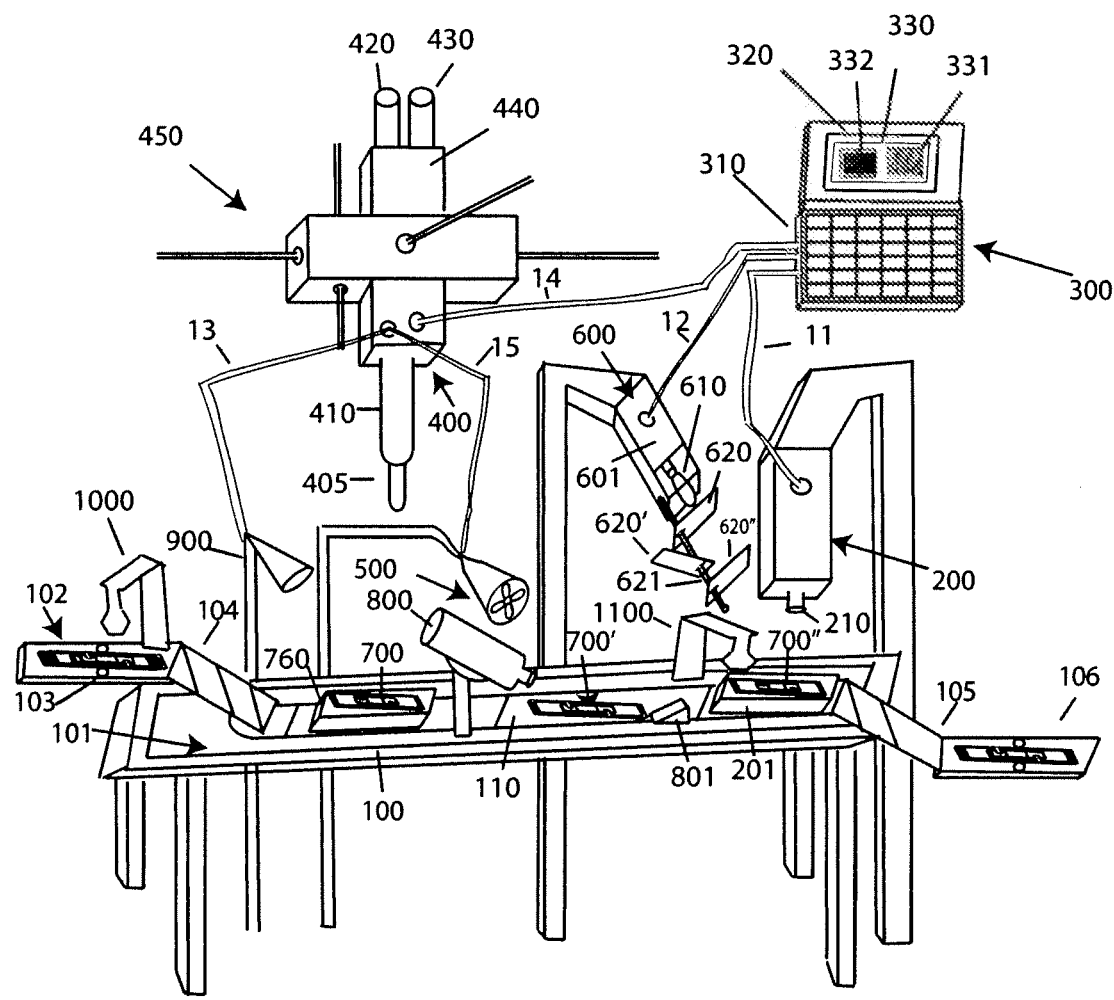
FIG. 1A: is a perspective, schematic view of a system for analyzing body fluids.

With reference to FIG. 1A, a system 10 for analyzing body fluids is disclosed. The system may comprise a platform 100, a light receiving device 200, a computer 300, an applicator 400, a gas circulation device 500, a light source 600, a dispenser 800, a discharge device 900, a slide labeler 1000, and slide label reader 1100. The following sections below include capitalized headings which are intended to facilitate navigation through the specification. The headings are not intended to be limiting of the invention in any manner.

The Platform 100

In embodiments which feature a platform 100, an advancer 110 may be configured to receive one or more slide apparatuses 700-700''. The advancer 110 may be attached to a surface, such as the top surface 101, of the platform. The advancer 110 may take the form of a belt as shown in FIG. 1A, the system may use a mechanical arm, gravity, magnetism, hydraulics, gears, or other locomotion techniques to move the slide apparatus along the surface 101 of the platform.

The platform 100 may also comprise a feeder 102 and a collector 106 for respectively feeding and collecting the slide apparatuses 700 from or to a stack or rack. The feeder 102 may be equipped with a feeder propulsion mechanism 103 (such as rubberized wheels) for pushing the slides down a ramp 104 onto the advancer 110. (Of course embodiments of the invention could be built without a ramp. For example, if the feeder is level with advancer 110, no ramp would be needed. Alternatively, a mechanical arm could be used to grab the slide apparatus 700 and place the slide apparatus 700 on the advancer directly.) Alternate mechanisms to propel the slide out of the feeder 102 may be used such as magnets or hydraulics. The feeder may comprise a sensor for determining how many slides are present. The sensor could measure the weight of the slide apparatuses 700 for example to determine how many slide apparatuses were present. FIG. 1A illustrates 3 slide apparatuses 700 stored in the feeder 102. The collector 106 may also comprise a sensor for determining how many slides are present in the collector 106. The sensor may inform the computer when a preset number of slides have been analyzed or may inform the computer of the receipt of a slide on an ongoing basis.

The Light Receiving Device 200

The light receiving device 200 may be a microscope (such as brightfield microscope), a video camera, a still camera, or other optical device which receives light. In embodiments using a standard brightfield microscope, one containing an automated stage (a slide mover 201) and focus may be selected. In one embodiment, a microscope may be attached to a motorized stage and a focus motor attachment. The microscope may have a motorized nosepiece, for allowing different magnification lenses to be selected under computer 300 control. A filter wheel may allow the computer 300 to automatically select narrow band color filters in the light path. LED illumination may be substituted for the filters, and use of LEDs may reduce the image acquisition time as compared to the time required for filter wheel rotation. A 1600×1200 pixel firewire camera may be used to acquire the narrow band images.

In some cases, the light receiving device will receive light reflected off slide apparatus 700'' and store an image of that light. In some embodiments fluorescent emission from the cellular objects may be detected in the light receiving device 200. However, since the light emission source 600 can be positioned below the platform, the light emission source may direct light so that it passes through the platform 100 and the slide 701 into the light receiving device 200. The light receiving device may be connected to a computer through a link 11, and may be capable of X, Y, and Z axial movement (in other embodiments a motorized stage or slide mover 201 may provide X, Y, and Z movement.) The light receiving device may comprise a link 11 such as a wire as shown in FIG. 1A, or other wireless systems may be used. The light receiving device 200 and any of the other components may be interfaced with the computer 300 through a link (11-15) which may provide energy to the component, provide instructions from the computer 300 to the component, or allow the component to send information to the computer 300. Light receiving device 200 may contain pan, tilt, or locomotive actuators to allow the computer 300 to position the device 200 in an appropriate position. The light receiving device may contain a lens 210 which focuses the light. The light receiving device may capture black and white or color images. Alternatively, two or more light receiving devices could be used to divide the processing time associated with capturing the images. For example a low magnification image station could be followed by a high magnification image station. Similarly, in some embodiments, the system 10, platform 100, computer 300, or light receiving device 200 may direct a slide mover 201 to move the slide apparatus 700 in order to store images of all the cells in the slide. Using a slide mover 201 may be desirable, if for example, the field size of the light receiving device 200 is smaller than the specimen zone 710 (FIG. 3).

The Computer 300

The computer 300 may be a laptop as shown in FIG. 1A, or a server, workstation, or any other type of computing device. The computer may comprise a processor, a display 320, and interface 310, and internal memory and/or a disk drive. The computer 300 may also comprise software stored in the memory or on computer readable media such as an optical drive. The software may comprise instructions for causing the computer to operate the light receiving device 200, the applicator 400, the applicator controller 490, the fan 500, the platform 100, advancer 110, light source 600, dispenser 450 or 800, or any component connected to one of these components. Similarly, the computer may receive information from any of these components. For example, the software may control the rate of dispersal of slides from the feeder 102, and feeder 102 may inform the computer about the number of slides present. In addition, the computer 300 may also be responsible for performing the analysis of the images captured by the light receiving device. Through the analysis process, the computer may be able to calculate the number of a specific type of cell in a particular volume of blood, for example for blood, red cell, white cell, and platelet counts and other measured and derived components of the CBC such as: hemoglobin content, red blood cell morphology, or WBC differential could be calculated. The image analysis software may analyze each individual field and sum the total red and white cell counts. To calculate the total counts per microliter in the patient vial, the number counted on the slide is multiplied by the dilution ratio and volume of the sub-sample. Results of the counts, morphologic measurements, and images of RBCs and WBCs from the slide may be shown on the display 320. In some embodiments, the computer 300 may be able to display numerical data, cell population histograms, scatterplots, and direct assessments of cellular morphology using images of blood cells displayed on the monitor. The ability to display cellular morphology provides users of the system 10, the ability to quickly establish the presence or absence of abnormalities in cell morphology that may warrant preparing an additional slide for manual review by an experienced technician or other professional. The software may provide the computer instructions to display images 331 received from the light receiving device or may cause the display 330 to show the results 332 (in perhaps a chart or graph for example) of an analysis of the images. Similarly, the computer 300 may be able to enumerate the number of cells of a specific type in a particular blood volume or enumerate the number of damaged cells, cancerous cells, or lysed cells in a particular volume of blood. The memory of the computer may contain software to allow the computer to perform the analysis process. The computer may use one or more magnifications during the analysis.

Although shown as one component, computer 300 may comprise multiple computers and a first computer could be used for controlling the components and a second computer could be used for processing the images from the light receiving device 200. In some embodiments, the various computer may be linked together to allow the computer to share information. The computer 300 may also be connected to a network or laboratory information system to allow the computer to send and receive information to other computers.

The Applicator 400

The applicator station includes 1) a precision automated dispenser tip that allows very small volumes of fluids to be handled and 2) automated movement of a substrate under the tip to allow the volume of fluid, e.g., diluted blood, to be dispensed over a defined area of the substrate.

In certain embodiments, the applicator 400 may comprise a syringe, a manual or motor driven pipettor or using a motor controlled pump attached through a tube to a pipette tip. While many different types of pipettes or syringes could be used, test results have shown improved results can be obtained through using an applicator 400 having better than 2% accuracy. The pump may be a peristaltic pump, a syringe pump, or other similar device that allows small volumes to be aspirated and dispensed through an orifice. Typically such an orifice will be contained in a tip 405 that is two to five millimeters in outside diameter with an inner diameter of 0.5 millimeters. The tip 405 may be disposable or washable. The tip 405 may be rounded to facilitate insertion and cleaning of the tip. Fluid flow through the tip is controlled to allow a thin layer of blood or diluted blood to be deposited onto the slide. By optimizing flow rate through the tip and the relative speed and height of the tip over the slide an appropriate density of cells can be deposited onto the slide. Each of these factors influences the other, so the proper combination of height, flow rate through the tip, and speed over the slide must be determined. In one embodiment the flow rate through the tip is 0.1 microliters per second while the tip is moving at a speed of 30 millimeters per second over the slide surface at a height of about 70 microns.

In use, the applicator 400 may comprise a known volume of body fluid such as 30 microliters (ul). The applicator may mix this fluid with a stain or diluent, and eject a portion of this fluid onto the slide apparatus 700 (particularly the specimen zone 710, FIG. 3). A typical sub-sample would be an aliquot of approximately ½ µl to 2 µl, but may be in the range of ¹⁄₁₀ to 10 µl. In some embodiments, the system 10 or applicator 400 may contain a first reservoir 420 for storing the body fluid and a second reservoir 430 for storing diluent. In some embodiments the body fluid will not be diluted.

The system 10 or applicator 400 may contain one or more dispensers 800. The dispenser 800 (or 450 in FIG. 1B) may be used to direct a fixative or a stain onto the slide 701. In this embodiment, the applicator 400 may contain one or more fluid chambers 410 to eject body fluid, diluent, stain, and fixative from the applicator 400. Some dispensers may be able to store both fluids and direct them sequentially onto the slide, or in alternate embodiments, two dispensers may be used (one for the fixative and one for the stain.) Excess stain and fixative may be removed from the slide, by tilting the slide apparatus so that it is orthogonal (or angled) to the platform surface 101. A slide tilter 801 may be used for this purpose. Slide tilter may comprise a simple wedge as shown, or may comprise a mechanical arm to tilt the slide.

In the embodiment shown in FIG. 1A, the stain dispenser is attached to the platform 100. Examples of stains compatible with embodiment shown in FIG. 1A may include: Wright-Giemsa stain, Geimsa stains, and Romanowsky stains. Other solutions that could be dispensed are fixatives (methanol) and buffer solutions. Other visualization methods involving immunocytochemical reagents or other markers of specific cell components may also be used. The stain dispenser may also be embodied as a stain reservoir 450 and attached to the applicator 400 (see FIG. 1B). Examples of stains compatible with the embodiment shown in FIG. 1B may include: Romanowsky stains, reticulocyte stains, and stains using specific antibodies. In the embodiment having dispenser 800, the dispenser can dispense stain onto the slide apparatus (particularly the specimen zone 710.) Dispenser 800 may take the form of a peristaltic pump. In the embodiment having a stain reservoir 450, the stain may be mixed in with the body fluid and the diluent from reservoirs 420 and 430. The body fluid and the diluent may be mixed together by a mixer 440, which can mix the fluid and diluent in certain ratios. In an alternate embodiment, the slide could be immersed into one or more baths of the fixation and staining solutions. In another embodiment, fixation and staining solutions could be moved across the slide using capillary action.

Various fixatives and diluents may be used with the present invention. For example 85% methanol can be used as the fixative. For some stains an ethyl alcohol or formaldehyde based fixative might be used. Diluents useful for diluting whole blood for example, may include salt solutions or protein solutions. Salt solutions range from "physiological saline" (0.9N), to complex mixtures of salts, to the commercial preparation Plasmalyte that simulates virtually all the salts found in human blood serum. Protein solutions can range from simple solutions of bovine albumin to Plasmanate, a commercial preparation with selected human plasma proteins. Such preparations can vary in protein concentrations, buffers, pH, osmolarity, osmalality, buffering capacity, and additives of various types. Synthetic or "substitute" versions of these solutions may also be usable, including Ficoll or Dextran or other polysaccharides. Other substitutes may be used. An example of a diluent is Plasmalyte plus Plasmanate in the proportion of 4:1 (Plasmalyte:Plasmanate). Another example of a diluent is 5% albumin. When analyzing whole blood, a dilution of 2 parts blood to 1 part diluent can be used, where the diluent is a physiologically compatible solution, but a range of dilution from 0:1 (no dilution) to 10:1 (diluent:blood) may be used in alternate embodiments.

The applicator may comprise a hydraulic piston for pushing the fluid out of fluid chamber 410 (like a syringe or a pipette). A tip 405 may be provided for adjusting the flow rate of the fluid. While size of the tip does not affect the speed (μl/sec) in which the solution flows out of the tip, generally, the smaller the opening in the tip, the greater the force (μg*distance/seconds$^2$). Additionally, the size of the tip affects thickness of the fluid flows 750 shown in FIGS. 2 and 3. A tip having a 0.3 millimeter inner diameter may provide for a flow rate of 0.1 microliters per second, and the distance from a middle point 751 of the first flow to the middle point 752 of the second flow may be 500 microns. In order to create the flows 750 shown in FIGS. 2 and 3, the system 10 may be configured to account for the variances in the number of cells in a given blood specimen. For human peripheral blood samples, the range is large but within one order of magnitude. In order to accurately count the blood cells, the overlap between red blood cells should be minimized. One method to provide minimal overlapping between cells is to lay down non-touching rows of cells from the tip of the applicator. Increasing viscosity of the diluted fluid or the type or amount of diluent may affect the width of the final settlement positions of the flows 750. By selecting a distance between rows to allow for the typical variation in blood samples, all cells can be counted in all samples. For many samples these gaps will be seen between the flows; however this does not affect the image analysis and the row and gap effect tends not to be noticed during high magnification manual review under the microscope. To avoid these gaps, a light receiving device could be attached to the applicator or positioned near station A (see FIG. 7A) to allow the computer 300 to determine the width of the first flow 751 (FIG. 3) formed by directing the cells onto the slide. By determining the width of the flow, i.e. how far the blood flows sideways from location the fluid was placed on the slide, the computer 300 could cause the applicator to adjust the gap size of the flows. The computer 300 calculate the distance the second flow 752 (FIG. 3) needs to be from the first flow 751, and place the flows so that they settle adjacent to one another minimizing the formation of any gaps between the flows. Using this process, a gapless or contiguous flow of cells can be applied to the specimen zone 710.

To physically place the cells on the slide 701, the computer 300 could direct the applicator controller 490 to perform the body fluid application process 7B (see FIG. 7B) which involves moving the body fluid chamber 410 in the X, Y, or Z directions to position the tip 405 so that it tracing the eventual locations of the flows 750. In some embodiments, the X, Y, and Z directions are all perpendicular to each other affording the applicator the ability to move in any direction in a three dimensional coordinate system.

The computer 300 may be connected to the applicator controller 490 to control this movement. In the embodiment shown in FIG. 3, the controller may position the tip at the top left corner of the specimen zone 710 and proceed to place fluid sample onto the cells by ejecting the fluid from the fluid chamber 410. While the ejection is occurring, the controller 490 may move the tip in the positive X direction to the top right portion of the specimen zone 710 (see FIG. 3). Once the top right section is reached, the controller 490 may move the tip in the negative Y direction one flow width. The flow 750 width may range from 300 to 1000 microns, and flow thickness increases as the flow rate of fluid out of the tip increases and/or the speed of the tip across the slide decreases. Additionally the viscosity of the fluid and diluent choice may affect the width of the flow 750 (FIG. 3). Typically, the cells of the fluid will settle within a few seconds once placed on the slide. Once the tip has been moved one flow width, the controller may move the tip in the negative X direction to the leftmost side of the specimen zone 710. Once the leftmost side is reached, the tip again may be moved one flow width in the negative Y direction. This process may be repeated until the entire specimen zone is covered. In alternate embodiments, the diluted body fluid could be applied to slide with a fixed applicator and slide which moves via the moveable slide controller 760 (this application process 7A is shown on FIG. 7A.) The slide controller 760 may be moveable in the X, Y, Z direction to move the slide apparatus in similar positions to allow the applicator to place flows 750 of body fluid on the specimen zone 710.

The number of cells placed on the slide 701 using this method will vary depending on the type of fluid being examined and the dilution ratio. Assuming whole blood were being analyzed with a 1:3 (blood:diluent ratio), about 900,000 red blood cells, 45,000 platelets, and 1,000 white blood cells would be placed on the slide. Though FIG. 3 shows the generation of a uniformly distributed fluid specimen in a rectangular shape, other shapes may be constructed in a similar manner. FIG. 4, shows for example, a fluid flow comprising a plurality of concentric circles. Like FIG. 3, the fluid flows 750 are placed adjacent to one another to create a uniform viewing field. This process provides a highly uniform distribution of cells across the specimen zone 710, facilitating the analysis process. Additionally, the computer 300 can alter the appearance and width of the fluid on the zone 710. For example, the computer 300 may control the speed at which the tip moves across the specimen zone, which would affect the thickness of the fluid resting on the zone. In some embodiments, speeds of 10 to 100 mm/s may be selected in order to provide the zone with a specimen which is about one cell thick. The controller 490 also may select the height of the tip above the slide 700. A height of 70+/−40 microns above the slide may be used in order to minimize damage to fluid cells when they come into contact with the slide apparatus 700, and to maintain fluid flow from the tip to the substrate.

The Gas Movement Device 500

Gas movement device 500 may comprise a fan (such as shown in FIG. 1) or may comprise other gas movement devices such as a compressor or a bellow for example. Gas movement device 500 may be connected directly to the computer 300 or may be connected through another component such as the platform 100 or the applicator 400 (as shown.) The gas movement device pushes gas (in some cases atmospheric air) across the slide to control the rate at which the slide dries. Moving too much air too quickly (i.e. too high of a fan speed) across the slide can cause cells in the specimen to burst due to too rapid drying, and too little air too slowly (i.e. too low of a fan speed) across the slide can cause the cells to dry too slowly and appear to shrink. The computer 300 may select the amount of air that moves across the slide in a period of time (i.e. the cubic feet of air per second) based upon the distance the gas movement device is from the slide, the type of fluid being analyzed, the width of the flows, and averages thickness of the flows (this would be the amount cells in each flow in the Z direction). The gas movement device 500 may be placed near the slide apparatus 700, and positioned so that the device directs gas so that the gas strikes the slide at an angle of 30-60° angle (45° degrees can be used) for a period of about 15 to 20 seconds. In some embodiments, the computer can control of humidity and temperature settings in the vicinity of the system to allow the drying process to occur without the use of a gas movement device 500.

The Light Emission Device 600

Two different embodiments of light emission device 600 are illustrated. In FIG. 1A, light emission device 600 comprises a housing 601, a multispectrum light source 610, a number of light filters 620, 620', and 620", and a filter selector 621. As shown in FIG. 1A, a portion of the housing has been removed to better show the light source 610. Light source 610 may comprise a white light source or other multispectrum light source such as a halogen bulb, florescent bulb, or incandescent bulb etc. Filters 620-620" may be used to filter the multispectrum light into a single wavelength or a narrow band of wavelengths. The filter selector 621 may select which filters appear in front of the light source 610. In some embodiments more than one filter may be used to allow a particular range of light to illuminate the slide. Filter selector 621, may comprise a rotation motor and a rod to spin the filters in and out of the path of the light. In a second embodiment light source may comprise one or more lasers or LEDs (630) which emit a narrow band of light (see FIG. 1B). An advantage for using LEDs in this system 10, is that LEDs can rapidly be switched on and off, allowing the light receiving device a single black and white camera to acquire the multiple spectral images in a very short time. LEDs also produce narrow bandwidths of illumination, typically from 15 to 30 nm full width at half maximum (the breadth of the wavelength intensity distribution at half of the peak brightness of the maximum intensity). Also, LEDs in the visible range do not project heat-producing infrared energy into the optical system and are relatively long lived as compared to conventional lamps. An advantage of using narrow-band illumination rather than unfiltered white light (i.e. broad-band illumination) is using narrow band illumination increases the sharpness of the images generated by the light receiving device 200. If the light receiving device 200 contains a lens, the presence of the lens may cause some chromatic aberration that result in slight focus shifts or image quality degradation when using different colors. With white light illumination this can result in an overall degradation of the image quality. The light receiving device 200 may capture a black and white image for each narrow-band of illumination. The computer 300 may be able to correct focus and image quality for each wavelength by adjusting the focal distance or the distance of the lens from the slide. In some embodiments, the computer 300 may shift the focus position of the lens while a number of light colors are emitted sequentially to improve the quality of the image.

Various wavelengths of light may be directed by the light emission device 600. Two-eight or more different wavelengths of light may be directed at the slide apparatus 700. Wavelengths such as 430 nm are useful for imaging a hemoglobin-only image for assessing RBC morphology and hemoglobin content. Using an image taken with such a wavelength which is designed to show only red blood cells, it may also show red blood cells which are touching white blood cells. The touching red blood cells may be digitally removed from images to make it easier for the computer to detect the white blood cell borders in order to make more accurate cellular measurements and enumeration. Light emitted at 570 nm may be useful to provide high contrast images for platelets and nuclei. Other wavelengths may be chosen in order to best discriminate the colors of basophils, monocytes, lymphocytes (all shades of blue), eosinophils (red), and neutrophils (neutral color). For counting platelets, for example, two colors of illumination may be used (such as 430 nm and 570 nm). A high contrast image may be obtained by subtracting the 430 nm image from the 570 nm image. Light having a wavelength of 430, 500, 525 and 600 are particularly effective at showing cell color information, but light at wavelengths between 400 nm and 700 nm inclusive may be used. These wavelengths will also be used for the display of the color images if appropriate. Otherwise one or two additional images may need to be taken for the 200+ cells that will be analyzed for the differential count and which may be shown on the display 320. Typically the narrow-band images will be chosen from the range of 400 nm to 750 nm. Test results have shown that 2-8 separate light colors to work well, with 3-4 separate light colors being optimal. The computer 300 may be able to further refine the images by compensating for spatial shifts. Also the computer may combine the various colored images to generate multi color images for display or analysis. Numeric descriptors of the individual images or combined images can be used to determine spatial, densitometric, colorimetric and texture features of the cells for classification of the cell types. A further advantage of using narrow band illumination is that using narrow band illumination allows for the elimination of the use of oil objectives or coverslips. Light is refracted when the light passes from glass to air. Prior art systems have used oil objectives or coverslips to minimize this refraction at air to glass transitions, but having to add oil or coverslips adds steps to processing the slides, and increases the per slide analysis cost. To overcome, the need to use coverslips or oil, a combination of narrow band LEDS or filtered light can be used. Reducing the variance or bandwidth in the wavelengths of the light decreases the distortion in the image captured by the light receiving device 200 when the light passes through the slide 701. The computer 300 may also instruct the light emission device 600, to focus the light from the light source (either 610 or 630) so that the light is properly focuses on the slide. To do this, the computer 300 may instruct a focus adjustor to optimize the focus for each color of light.

The Slide Apparatus 700

Figure 2:
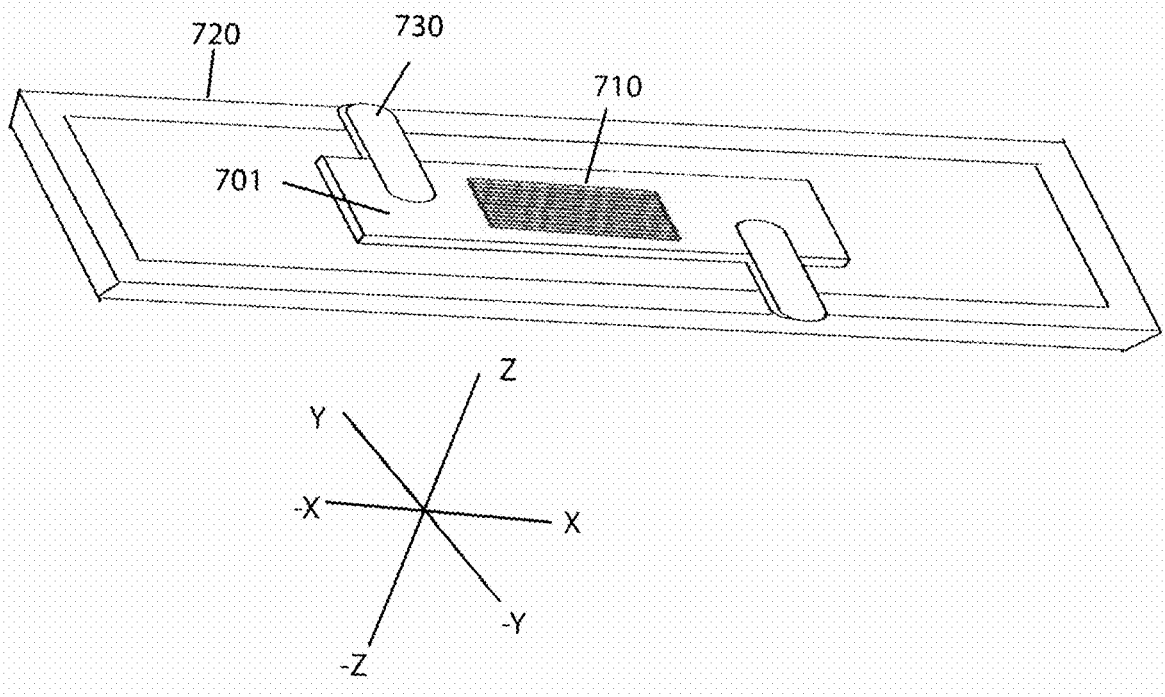
FIG. 2: is a perspective view of a slide and slide holder.

FIGS. 1A, 2, and 3 illustrate an embodiment of the slide apparatus 700 comprising a slide 701, a specimen zone 710, a slide frame 720, and a slide holder 730. However, other embodiments of the invention may not require the use of a slide holder 730 or slide frame 720. Additionally the specimen zone 710 boundary mark is optional as well, and may comprise one or more hydrophobic rings or other painted marks. These rings may help contain the blood sample, and also make reviewing images of the slides easier by quickly locating the specimen zone when a slide is viewed manually under a microscope (the may also assist the analysis process in interpreting the image.) The rings may also assist in facilitating the transfer of the stain onto the slides. Additionally, while the specimen zone has been illustrated as a rectangle other shapes such as a circle or triangle may be used. Different size specimen zones may be used, including zones having a total area of one half to three square centimeters. The slide 701 may be manufactured from glass or plastic and may be 1 inch tall by 3 inches wide by 1 mm thick. Also shown on FIGS. 2 and 3 is a fluid sample dispersed on the slide in flows 750. The fluid can be dispersed in flows as shown in FIG. 3, or in a spiral pattern as shown in FIG. 4.

The Discharge Device 900

Figure 1B:
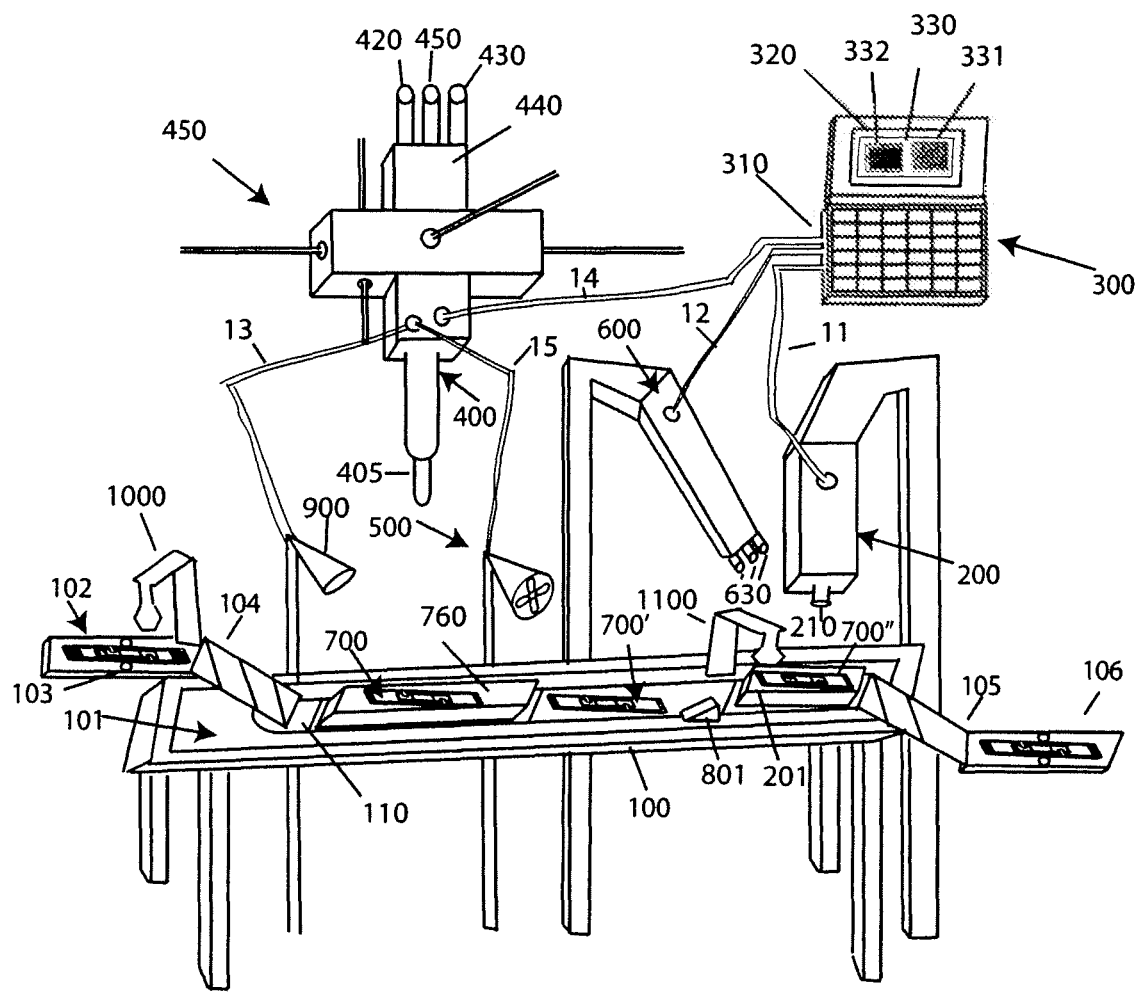
FIG. 1B: is a perspective, schematic view of a system for analyzing body fluids.

With reference to FIG. 1B, the system may comprise a discharge device 900 for pretreating the slide 701. The discharge device may take the form of a corona discharge device. The discharge device 900 may clean the slide 701 by creating a high intensity heat to burn off small particles to clean the slide to create a hydrophilic surface. Electro-Technic Products, Sawicki Pa. makes a corona discharge device compatible with the present invention. To perform the pretreatment, the computer 300 would turn on the discharge device 900, and cause the slide apparatus controller 760 to move the slide in a spiral or raster motion for about 15 seconds (though a range of 1-20 seconds could be used.) The discharge device may be set at an angle from the slide, or may be positioned directly above the slide. Typically, the discharge device 900 may be positioned approximately 10 to 20 mm above the slide.

The Slide Labeler 1000 and Slide Label Reader 1100

The system 10 may optionally include a slide labeler 1000 and optionally a slide label reader 1100. The slide label reader 1000 may situated on the platform 100 near the feeder 102 as shown in FIGS. 1A and 1B or may be free standing or attached to other components. Slide labeler 1000 may place a label on the slide. A label 770 may include items such as stickers, barcodes, RFID tags, EAS tags, or other type of markings on the slide. FIG. 3 shows an exemplary slide having a UPC bar code label on it, but other markings conventions may be used. Moreover, the markings may be applied directly to the slide via paint or ink, or may they may be stuck to the slide using a writing medium and an adhesive (like a sticker).

The system 10 may comprise a slide label reader 1100. Slide label reader 1100 may read markings placed on the slide from the slide labeler 1000 or by labelers external to the system. The slide label reader 1100 could comprise an interrogator, a bar code reader, or other optical device. In some embodiments, the system 10 may be able to determine information from the labels 770 without a slide label reader 1100 by using the light receiving device 200 to capture an image of the label 770. The computer 300 or the light receiving device (if it contains a processor and memory) could perform imaging processing on the image containing the label and determine the information about the label 770.

Bone Marrow

As discussed above, the present invention may be used to analyze peripheral or whole blood. The invention can also be used, however, to study cells of various types of body fluids. For example, the preparation methods and analysis techniques described here can also be applied to bone marrow aspiration samples. Bone marrow samples have a higher cellular density and contain many immature red and white blood cell types that are seldom found in peripheral blood. The technique of preparing a thin layer of cells, staining with a Romanowsky stain and analyzing with image analysis can be applied to bone marrow aspirates as well, however more sophisticated image analysis may be needed to discriminate the additional types of cells.

As with peripheral blood samples, bone marrow samples may be collected into a container with an anticoagulant. This anticoagulant may be EDTA or heparin. Additional diluting or preserving fluid may be added to the sample. In the instrument described here a bone marrow sample would be prepared by first agitating the sample to provide a thorough mixing. Due to the uncertain cellular density of such samples one or more dilutions may be prepared and pipetted onto the slide or slides. In one embodiment, a triple dilution process may be used to create three specimens. A first specimen may be created by adding 2 parts diluent to one part bone marrow. The first specimen may then be ejected onto a first portion of the specimen zone 710 of the slide 701. A second specimen may be created by adding four parts diluent to the bone marrow. The second specimen may then be ejected onto a second portion of the specimen zone 710 of the slide 701. A third specimen may be created by adding eight parts of diluent to the marrow. The third may then be ejected onto a third portion of the specimen zone 710 of the slide 701.

For the image analysis, a low magnification assessment of the cellular area on the slide could choose the optimum one third for subsequent analysis. Once the proper area of the slide is selected, 200+ bone marrow cells would be measured to determine the differential count.

Reticulocytes

The system 10 may also count the number of reticulocytes in a blood sample. Using a Romanowsky stain to mark RNA, the computer 300 can count the number of reticulocytes present in the specimen. When a Romanowsky stain is used, the reticulocytes appear slightly bluer than other red blood cells, and are usually slightly larger. The computer 300 can use its analysis process (16A or 17B, of FIGS. 7A and 7B) to quantify the blue component of the red cells. The analysis process could measure integrated optical density of a cell's difference image created by subtracting one image taken with blue light of 430 nm (range of 400 to 470 nm) from an image taken with non-blue light of 600 nm (range of 470 to 750 nm). The analysis process could correlate the number of red blood cells with a defined range of integrated blue component to a number of reticulocytes counted manually or by flow methods using special stains. The accuracy of the analysis process can be further improved by requiring the analysis process (16A or 17B) to measure the size, shape, color, and measured characteristics of cellular objects. For example, the analysis process could detect the difference between a red blood cell with a bluish platelet lying under or over a red blood cell as opposed to a true reticulocyte.

Process Flows

Figure 7A:
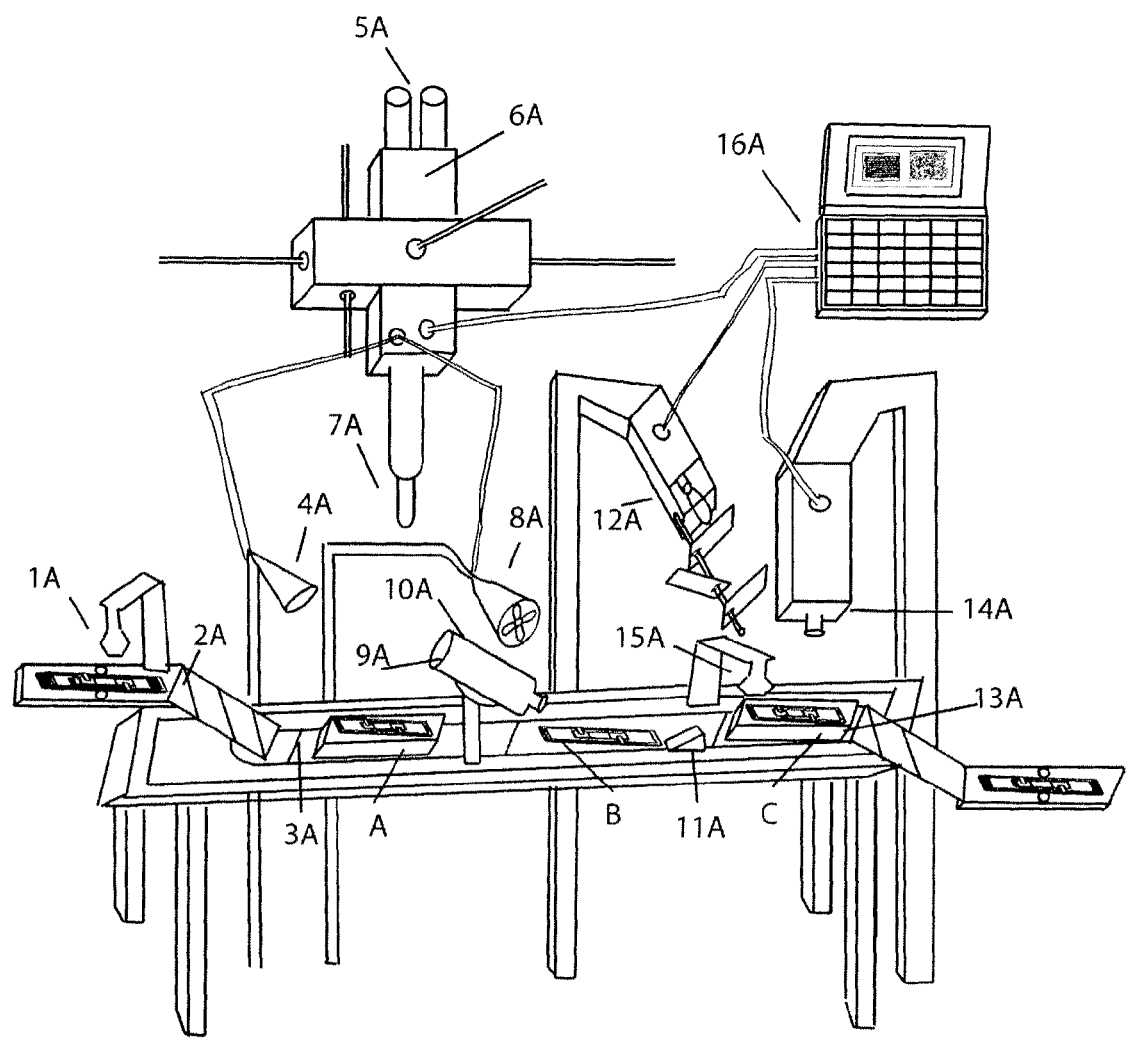
FIG. 7A: is a process flow schematic of the embodiment shown in FIG. 1A.
Figure 7B:
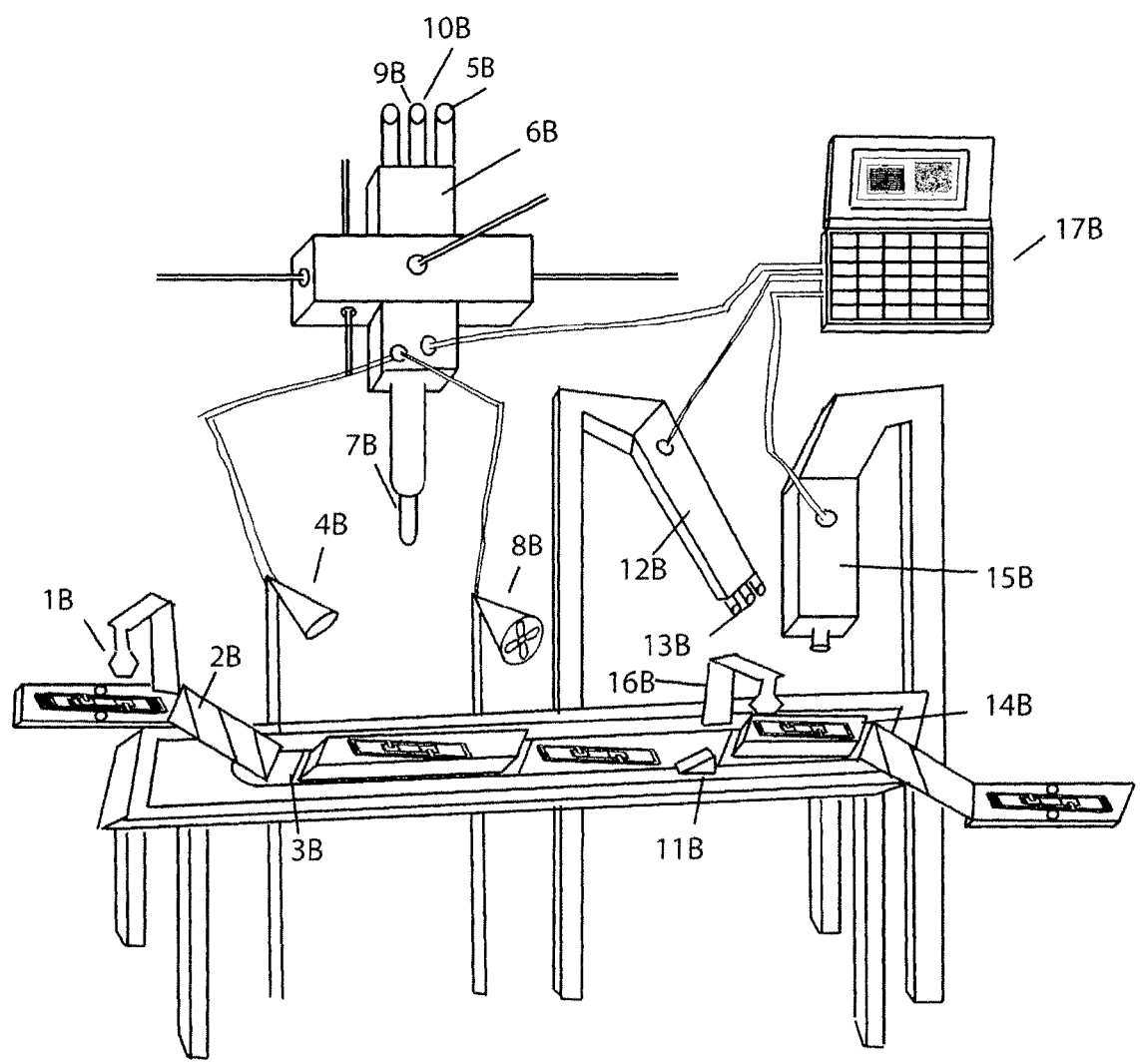
FIG. 7B: is a process flow schematic of the embodiment shown in FIG. 1B.
Figure 10:
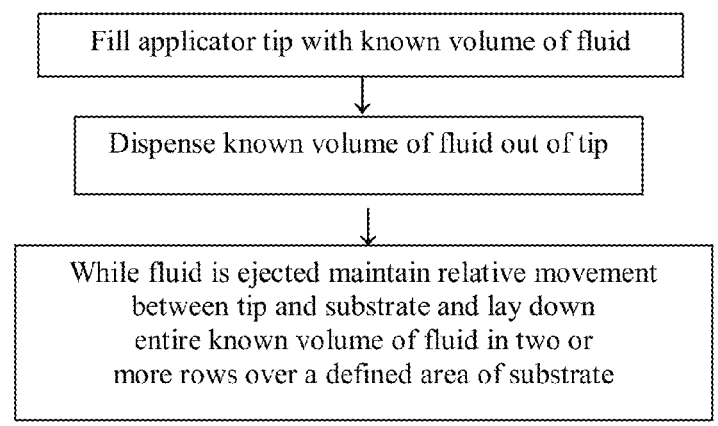
FIG. 10 is a flow chart of process steps carried out by the systems described herein.

Embodiments of the present invention are contemplated to process multiple slide apparatuses 700 in a pipelined series as shown in FIG. 1A or 1B, but embodiments that process the slide apparatuses 700 in parallel may also be constructed. Embodiments may be constructed that can process a large number (e.g., 10-20) of slide apparatuses in series or in parallel, or smaller volume systems 10 can be constructed (processing 4-8 slides at a time). The following two paragraphs describe an example of a process flow for FIGS. 1A and 1B, but alternate process flows are possible and feasible. These process flows are also illustrated in FIGS. 7A and 7B, and generally in FIG. 10. Additionally, other configurations of the system are possible, and would likely have different process flows. Moreover, although the steps are presented in a series, many of the steps may be presented in a different order or performed simultaneously. Finally, most of the following steps are optional, and may be removed from the process flow.

In the embodiment shown in FIGS. 1A and 7A, the software stored in the memory of the computer 300 may cause the computer to control the order, speed, and variables associated with processes 1A-16A. The process may begin with computer 300 sending an instruction to the slide labeler 1000 to place a label 770 on the slide 701. The labeling process 1A may be performed in the feeder 102 or may be performed on the ramp 104 or at the slide apparatus controller 760. To move the slide apparatus 700 from the feeder 102, the computer 300 may send an instruction to the feeder 102 to activate the feeder propulsion mechanism 103. The computer 300 may also cause a feeder process 2A to begin which may include moving the slide apparatus 700 onto the advancer 110. The feeder process may include utilizing the sensor to determine how many slides are in the feeder 102. The computer may cause the advancer 110 to initiate an advancing process 3A including moving the slide to the application station A, and onto the slide apparatus controller 760 (if one is present). Once the slide apparatus is on the slide apparatus controller, the slide may be pretreated by the discharge device 900. The pretreatment process 4A may include the slide controller 760 rotating or spinning the slide apparatus 700 as the discharge device burns debris off of the slide 701. Once the optional pretreatment process 4A is completed the applicator process 5A may begin. The applicator process 5A may comprise having an operator fill the reservoir tank 420 with diluent and reservoir tank 430 with body fluid. Body fluids such as peripheral blood or bone marrow aspirate may be used. Alternatively, the fluids may be aspirated automatically from a patient's sample vial. The mixer 440 may begin the mixing process 6A to mix the diluent with the body fluid in a certain ratio such as 2:1 (body fluid:diluent) to form a diluted body fluid. To apply the diluted body fluid to the slide 701, one of two body fluid application processes 7A or 7B (FIGS. 7A and 7B, described above in conjunction with the applicator 400) may be performed (but either process could be used for both embodiments.) After the application completes, the advancer 110 may continue the advancing process moving the slide apparatus to a preparation station B. Once the body fluid application process 7A is completed, the drying process 8A may begin. The drying process may include using the gas movement device 500 to direct gas onto the slide for a period of time (such as 20-30 seconds). Once the slide is dried, the body fluid may be fixed using the fixation process 9A. After the body fluid is fixed, it may be stained using the staining process 7A. After the body fluid is stained, the excess stain may be removed using a stain removing process 11A. The stain removing process 11A may include a slide tilting process wherein the slide is tilted at least partially in order to allow the stain and or fixative to drain off the slide. To capture images of the specimen, the advancer 110 may continue advancing the slide apparatus to the imaging station C. At the imaging station C, the system may activate specimen illuminating process 12A and an imaging process 15A, which uses the light emission device 600 and light receiving device 200 respectively to illuminate the specimen and to capture images of the illuminated specimen. The computer 300 may direct the light emission device to apply to different filters to the light to change wavelength of emitted light using the light filtration process 13A. Alternatively, the LED illumination process of 13B could be used if a light emission device 600 comprising LEDs is provided. A slide movement process 14A may be performed by the slide mover 201 to position the slide 701 in various X, Y, Z directional positions. Since in many embodiments, the magnification of the lens of the light receiving device will generate a view field which only contains a part of the total area of the specimen, the slide movement process 14A may be utilized to move the specimen into different X, Y positions allowing the light receiving device 200 to take multiple images 331 to capture the entire specimen. The slide mover may also be able to move the slide to multiple imaging stations allow light receiving devices to take images at various magnifications. The slide mover may also be able to move the slide in the Z direction to allow the light receiving device to take images at various magnifications. The system 10 may use the label reader 1100 to read the labels on the slides (using the label reading process 16A), or alternatively the computer may recognize symbols on the label using image recognition software. The light receiving device may transfer the images to the computer through link 11. The computer may save the images in internal memory and use its software to analyze the images (using the analysis process 17A) to count the cells and perform calculations on the resulting data. The software may generate results including tables, charts, or graph of the results 332, and may display the images 331 on the display 320 of the computer 300.

A second process flow is shown in FIG. 7B (also refer to FIG. 1B). The process may begin with computer 300 sending an instruction to the slide labeler 1000 to place a label 770 on the slide 701. The labeling process 1B may be performed in the feeder 102 or may be performed on the ramp 104 or at the slide apparatus controller 760. To move the slide apparatus 700 from the feeder 102, the computer 300 may send an instruction to the feeder 102 to activate the feeder propulsion mechanism 103. The computer 300 may also cause a feeder process 2B to begin which may include moving the slide apparatus 700 down the ramp 104 onto the advancer 110. The feeder process 2B may include utilizing the sensor to determine how many slides are in the feeder 102. The computer may cause the advancer 110 to initiate an advancing process 3B including moving the slide to the application station A, and onto the slide apparatus controller 760 (if one is present). Once the slide apparatus is on the slide apparatus controller 760, the slide 701 may be pretreated by the discharge device 900. The pretreatment process 4B may include the slide controller 760 rotating or spinning the slide apparatus 700 as the discharge device burns off any debris on the slide 701. Once the optional pretreatment process 4B is completed the applicator process 5B may begin. The applicator process 5B may comprise having an operator fill the reservoir tank 420 with diluent and reservoir tank 430 with body fluid. Alternatively, the fluids may be aspirated automatically from a patient's sample vial. Body fluids such as peripheral blood or bone marrow aspirate may be used. The applicator 400 may contain a third reservoir for containing the stain, and perhaps a fourth reservoir for containing fixative (however, in other embodiments the stain and fixative could be stored in the same reservoir). The mixer 440 may begin the mixing process 6B to mix the diluent with the body fluid (and possibly the stain and fixative) in a certain ratio such as 2:1 (body fluid:diluent) to form a diluted body fluid. In these embodiments, the applicator 400 would apply the stain and or the fixative after the body fluid is applied to the slide using the staining process and fixative process respectively. Once the slide is dried, the body fluid may be fixated using the fixation process 9B. After the body fluid is fixed, it may be stained using the staining process 7B. To apply the diluted body fluid to the slide 701, one of two body fluid application processes 7A or 7B (described above in conjunction with the applicator 400) may be performed (but either process could be used for both embodiments.) Once the body fluid application process 7B is completed, the drying process 8B may begin. The drying process may include using the gas movement device 500 to direct gas onto the slide for a period of time (such as 20-30 seconds). After the body fluid is stained and fixed, the stain may be removing using a stain removing process 11B. The stain removing process 11B may include a slide tilting process wherein the slide is tilted at least partially in order to allow the stain and or fixative to drain off the slide. To capture images of the specimen, the advancer 110 may continue advancing the slide apparatus to the imaging station C. At the imaging station C, the system may activate specimen illuminating process 12B and an imaging process 15B, which uses the light emission device 600 and light receiving device 200 respectively to illuminate the specimen and to capture images of the illuminated specimen. The computer 300 may direct the light source 600 to apply a sequence of narrow band light onto the slide 701 using LED illumination process 13B. Alternatively, if a light emission device 600 with filters is provided, the computer 300 may direct the light emission device to radiate light and apply different filters to the light to change wavelength of emitted light using a light filtration process 13A. Once slides are illuminated, a slide movement process 14B may be performed by the slide mover 201 to position the slide 701 in various X, Y, Z positions. Since in many embodiments, the magnification of the lens of the light receiving device will generate a view field which only contains a part of the total area of the specimen, the slide movement process 14B may be utilized to move the specimen into different X, Y positions allowing the light receiving device 200 to take multiple images to capture the entire specimen. The slide mover may also be able to move the slide to multiple imaging stations allow light receiving devices to take images at various magnifications. The slide mover may also be able to move the slide in the Z direction to allow the light receiving device to take images at various magnifications. The system 10 may use the label reader 1100 to read the labels on the slides (using the label reading process 16B), or alternatively the computer may recognize symbols on the label using image recognition software. The light receiving device may transfer the images to the computer through link 11. The computer may save the images in internal memory and use its software to analyze the images (using the analysis process 17B) to count the cells and perform calculations on the resulting data. The software may generate results including tables, charts, or graph of the results, and may display the images 331 or the results 332 on the display 320 of the computer 300.

Test Results

To determine the accuracy of this method, computer algorithms were developed to count RBCs and WBCs from digital images.

Figure 8:
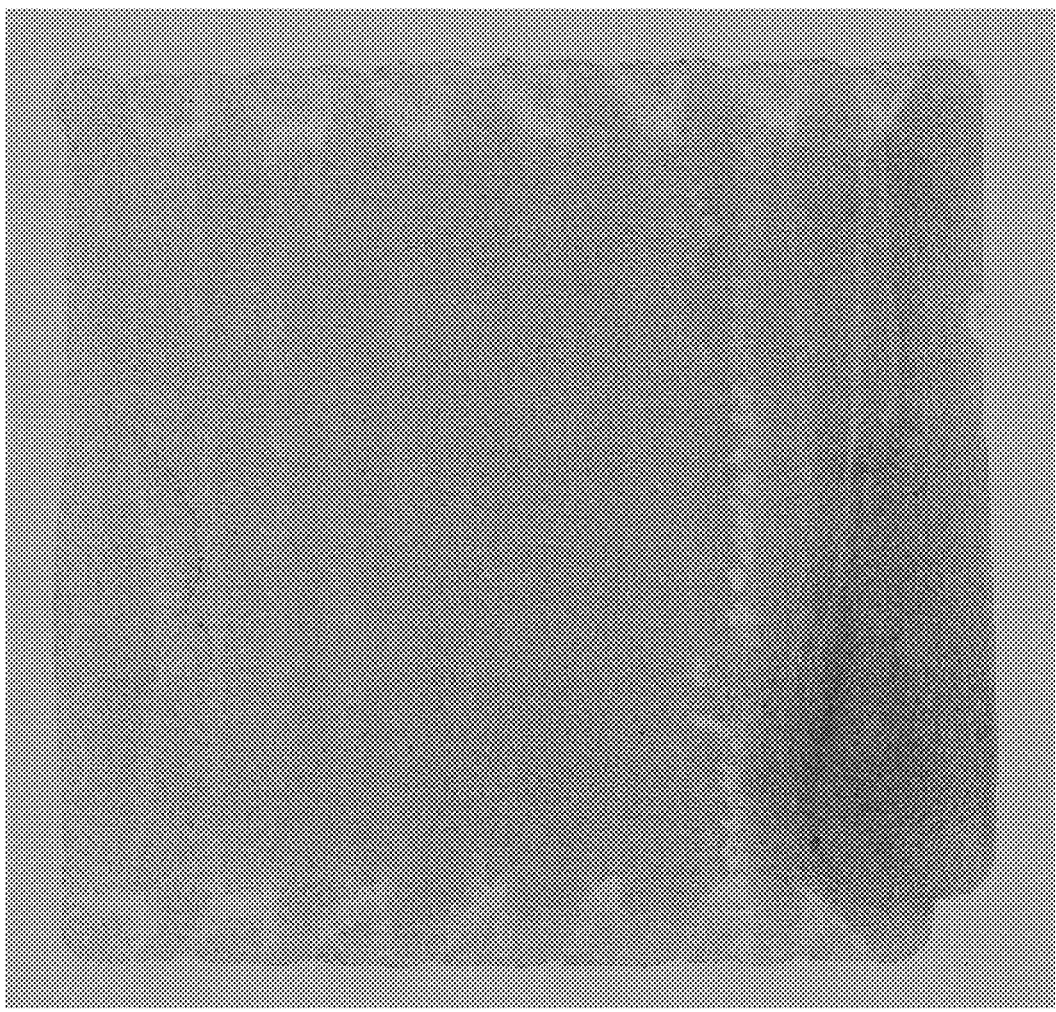
FIG. 8 is an image of rows of a blood sample distributed on a slide. The image was created by tiling approximately 450 individual images together while reducing overall image size.
Figure 9:
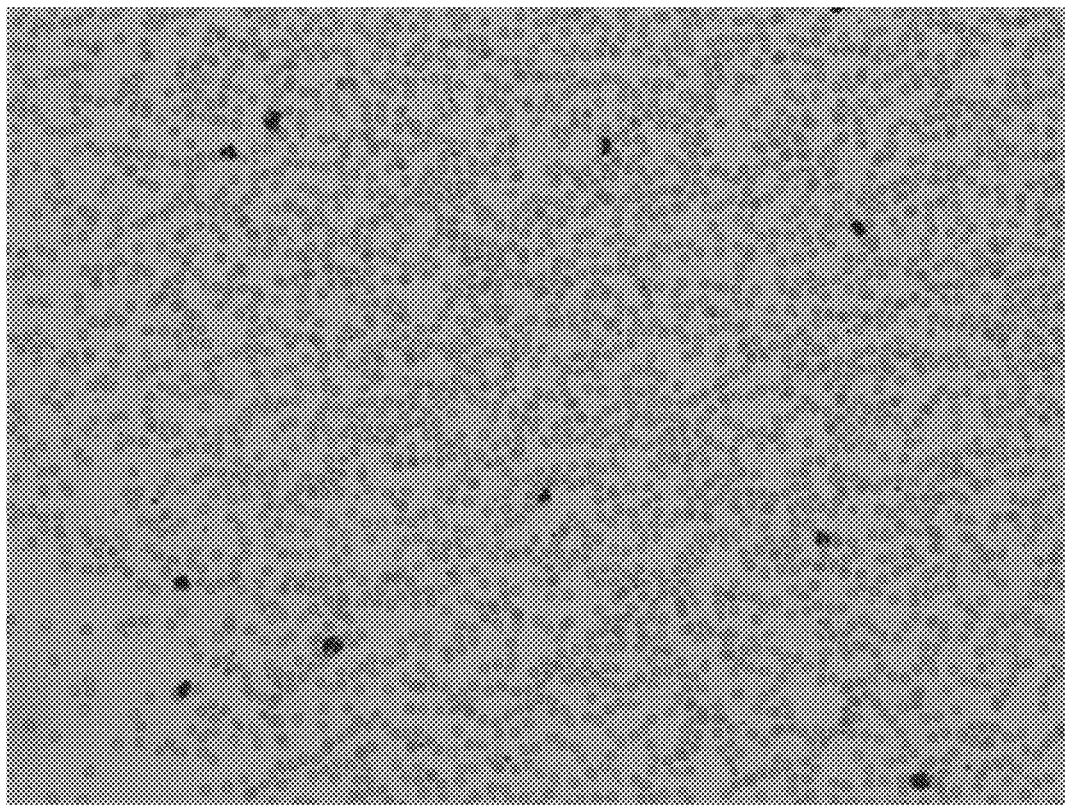
FIG. 9 is an image of blood cells distributed on a slide acquired by a digital camera for subsequent analysis.

The image shown in FIG. 8 is of rows of a blood sample distributed on a slide generated by an automated applicator system. The fields at the edges of the square sample contain fewer cells as the applicator tip quickly turns to lay down the next row. At the end of the last row, a "blob" of cells was created where the applicator tip stopped and lifted from the surface of the slide. In such crowded fields of cells, the software is still able to make an estimate of the red cell counts, although it appears that the computer counts may be slightly low in crowded areas. FIG. 9 shows the details of one digital image from the blood cell sample from which white blood cell and red blood cell counts were made.

An accurate count may be made by scanning the entire preparation for red blood cells and white blood cells, but an accurate platelet count might use a reduced number of fields, since an average cell deposition will have a total of around 30,000 platelets, or approximately 500 platelets per field. The image analysis programs then analyze each individual field and sum the total red and white cell counts. To calculate the total counts per microliter in the patient vial, the number counted on the slide is multiplied by the dilution factor.

Table 1 below shows a summary of data for 34 slides. "Invention" data represents red and white blood cell counts from slides produced using the method described above, and analyzed using image analysis counting algorithms. "Sysmex" data represents red and white blood cell counts from a commercial "flow-based" automated CBC analyzer. Note that the specimens include very high and very low red blood cell counts and white blood cell counts.

TABLE 1

| Specimen | Invention Count RBC × $10^6$ | Sysmex Count RBC × $10^6$ | Invention Count WBC × $10^3$ | Sysmex Count WBC × $10^3$ |
|---|---|---|---|---|
| 1 | 4.97 | 5.69 | 5.00 | 5.64 |
| 2 | 3.66 | 4.22 | 5.92 | 6.99 |
| 3 | 4.32 | 4.83 | 4.13 | 4.00 |
| 4 | 4.00 | 4.01 | 3.36 | 2.91 |
| 5 | 4.27 | 4.22 | 9.66 | 8.48 |
| 6 | 2.83 | 3.20 | 8.60 | 9.25 |
| 7 | 4.46 | 4.79 | 5.80 | 6.40 |
| 8 | 4.04 | 4.78 | 4.02 | 4.63 |
| 9 | 2.98 | 3.10 | 10.02 | 10.16 |
| 10 | 4.88 | 5.04 | 6.24 | 6.44 |
| 11 | 2.95 | 3.29 | 7.28 | 8.43 |
| 12 | 4.47 | 4.97 | 6.75 | 7.70 |
| 13 | 2.75 | 3.01 | 4.91 | 4.62 |
| 14 | 4.35 | 4.73 | 8.48 | 9.27 |
| 15 | 3.82 | 4.16 | 6.26 | 6.06 |
| 16 | 3.16 | 3.50 | 14.49 | 14.97 |
| 17 | 3.87 | 4.22 | 5.37 | 4.67 |
| 18 | 3.69 | 4.04 | 3.75 | 3.50 |
| 19 | 4.08 | 4.51 | 11.42 | 11.22 |
| 20 | 3.03 | 3.26 | 2.00 | 1.87 |

TABLE 1-continued

| Specimen | Invention Count RBC × $10^6$ | Sysmex Count RBC × $10^6$ | Invention Count WBC × $10^3$ | Sysmex Count WBC × $10^3$ |
|---|---|---|---|---|
| 21 | 3.23 | 3.49 | 6.68 | 6.50 |
| 22 | 4.35 | 4.63 | 10.09 | 9.95 |
| 23 | 2.84 | 3.03 | 10.28 | 11.62 |
| 24 | 3.02 | 3.27 | 0.59 | 0.57 |
| 25 | 2.75 | 2.87 | 17.06 | 16.42 |
| 26 | 2.78 | 3.01 | 5.80 | 5.56 |
| 27 | 2.73 | 2.90 | 8.84 | 8.28 |
| 28 | 2.97 | 2.98 | 17.18 | 17.41 |
| 29 | 3.56 | 3.75 | 16.70 | 16.79 |
| 30 | 2.91 | 3.16 | 7.05 | 7.89 |
| 31 | 3.32 | 3.55 | 9.80 | 9.73 |
| 32 | 3.01 | 3.29 | 45.00 | 44.62 |
| 33 | 4.77 | 5.24 | 6.11 | 6.44 |
| 34 | 4.34 | 4.57 | 7.01 | 6.89 |

Table 1 shows the raw data from counts performed on 34 vials. The second and third columns shows the red blood cell counts expressed as millions per microliter of patient blood for the invention count and the Sysmex count, respectively. The fourth and fifth columns shows the white blood cell counts expressed as thousands per microliter of patient blood for the invention count and the Sysmex count, respectively.

TABLE 2

Table 2. Table 2 shows the raw data from counts performed on 34 vials.

| Vial | SysmexRBCs | RBCcounts | RBCscaled | SysmexWBCs | WBCcounts | WBCscaled |
|---|---|---|---|---|---|---|
| 1 | 5.69 | 1241765 | 4.97 | 5.64 | 1250 | 5.00 |
| 2 | 4.22 | 915262 | 3.66 | 6.99 | 1481 | 5.92 |
| 3 | 4.83 | 1080856 | 4.32 | 4.00 | 1033 | 4.13 |
| 4 | 4.01 | 998828 | 4.00 | 2.91 | 840 | 3.36 |
| 5 | 4.22 | 1068411 | 4.27 | 8.48 | 2414 | 9.66 |
| 6 | 3.20 | 707250 | 2.83 | 9.25 | 2149 | 8.60 |
| 7 | 4.79 | 1115913 | 4.46 | 6.40 | 1451 | 5.80 |
| 8 | 4.78 | 1010933 | 4.04 | 4.63 | 1006 | 4.02 |
| 9 | 3.10 | 744241 | 2.98 | 10.16 | 2504 | 10.02 |
| 10 | 5.04 | 1220400 | 4.88 | 6.44 | 1559 | 6.24 |
| 11 | 3.29 | 736701 | 2.95 | 8.43 | 1819 | 7.28 |
| 12 | 4.97 | 1117506 | 4.47 | 7.70 | 1688 | 6.75 |
| 13 | 3.01 | 687645 | 2.75 | 4.62 | 1228 | 4.91 |
| 14 | 4.73 | 1086737 | 4.35 | 9.27 | 2120 | 8.48 |
| 15 | 4.16 | 955279 | 3.82 | 6.06 | 1564 | 6.26 |
| 16 | 3.50 | 789218 | 3.16 | 14.97 | 3622 | 14.49 |
| 17 | 4.22 | 967780 | 3.87 | 4.67 | 1343 | 5.37 |
| 18 | 4.04 | 922880 | 3.69 | 3.50 | 937 | 3.75 |
| 19 | 4.51 | 1019878 | 4.08 | 11.22 | 2855 | 11.42 |
| 20 | 3.26 | 757606 | 3.03 | 1.87 | 500 | 2.00 |
| 21 | 3.49 | 808679 | 3.23 | 6.50 | 1670 | 6.68 |
| 22 | 4.63 | 1086451 | 4.35 | 9.95 | 2522 | 10.09 |
| 23 | 3.03 | 709164 | 2.84 | 11.62 | 2571 | 10.28 |
| 24 | 3.27 | 753952 | 3.02 | 0.57 | 147 | 0.59 |
| 25 | 2.87 | 688731 | 2.75 | 16.42 | 4265 | 17.06 |
| 26 | 3.01 | 695059 | 2.78 | 5.56 | 1451 | 5.80 |
| 27 | 2.90 | 682449 | 2.73 | 8.28 | 2209 | 8.84 |
| 28 | 2.98 | 741274 | 2.97 | 17.41 | 4295 | 17.18 |
| 29 | 3.75 | 890278 | 3.56 | 16.79 | 4174 | 16.70 |
| 30 | 3.16 | 727660 | 2.91 | 7.89 | 1762 | 7.05 |
| 31 | 3.55 | 831027 | 3.32 | 9.73 | 2450 | 9.80 |
| 32 | 3.29 | 753365 | 3.01 | 44.62 | 11250 | 45.00 |
| 33 | 5.24 | 1193348 | 4.77 | 6.44 | 1527 | 6.11 |
| 34 | 4.57 | 1085941 | 4.34 | 6.89 | 1753 | 7.01 |
| | RBC Correlation (R^2) | | 97.95% | WBC Correlation (R^2) | | 99.70% |

The $2^{nd}$ column gives the reference (Sysmex) RBC counts, while the $3^{rd}$ column reports the automated counts from the microscope slide. The $4^{th}$ column scales the counts to million cells per microliter, assuming a 1:4 dilution. The $5^{th}$-$7^{th}$ column show the data for the WBC counts. At the bottom of the table are the calculated correlation coefficients (R-squared).

The data was obtained from 34 patient samples during two sessions of preparing slides. The data is representative of typical patients, although the tubes were selected from patients with a wide distribution of red and white cell counts. Most, if not all of the 34 samples, were obtained from specimens "archived" during the day in the refrigerator, and then pulled and prepared on the instrument in the late afternoon. Once the tubes were pulled, they were processed consecutively.

The algorithms were first validated by comparing manually counted microscope fields to the automated counts. There is a high correlation between the manually counted cells and the automatically counted cells.

High correlation between the two methods was found for both the red blood cell counts and the white blood cells counts (see Tables 1 and 2 and FIGS. 5 and 6). The graph of FIG. 5 shows the correlation between the Sysmex counts and the automated slide based counts for the red blood cells. The data points are tightly clustered and form a line that indicates that the numbers on the vertical axis (the invention counts) are similar to the numbers on the horizontal axis (the Sysmex counts). Typically for such data a correlation coefficient (R-squared) can be calculated to show the degree of agreement, where 100% would be perfect agreement. An, R-squared value of 97.95% was calculated for this red blood cell data, indicating a high degree of agreement and similar to what two different automated instruments might show. The graph shown in FIG. 6 shows the correlation between the Sysmex counts and the automated slide counts for the white blood cells. The raw counts varied between 147 and 11,250 white blood cells per slide. An R-squared value of 99.70% was calculated for this white blood cell data, indicating a high degree of agreement and similar to what two different automated instruments might show. This confirms that the novel approach to quantitative transfer of cells was successful and that automated cell counts from computer imaging yielded accurate results.

Exemplary Process for CBC and White Blood Cell (WBC) Differential

The following sequence of steps may be performed in any order and some steps may be omitted or replaced with other steps.

Step 1. Extract a known volume of blood from a tube filled with a patient's blood.

Step 2. Dilute the blood if necessary. For example, one may use 5% albumin in distilled water as a diluent.

Step 3. Spread a known volume of blood or blood plus diluent over an area on a glass microscope slide in a thin layer. The slide may be treated to produce a hydrophilic surface to spread the cells better. The slide may be treated to allow optimal adherence of the blood elements to the slide.

Step 4. Allow the slide to dry in the air, or assist the drying using light air or heat.

Step 5. Capture an image without a coverslip using a "dry" objective that is corrected for no coverslip, for example one may use a 10× or 20× objective coupled to a CCD camera. Determine the count in each image frame including Red Blood Cells (RBCs), and possibly White Blood Cells (WBCs), and platelets. One or more colors may be used, for example using a color camera or using narrow band illumination produced by an interference filter or LED. Measurement of hemoglobin content may be done at this time as well.

Step 6. Fix and stain the cells on the slide. Fixation may be a separate step or combined with staining.

Step 7. Capture an image of stained slide without coverslipping, using a "dry" objective, to count RBCs, WBCs, and platelets and hemoglobin. This step may be in place of or in conjunction with step 5.

Step 8. Perform WBC differential count from high resolution images acquired without a coverslip, using a "dry" objective, for example with a 40× or 50× objective that is not corrected for a coverslip. A color camera or multiple black & white images taken using color filters or using LED illumination may be used. This step may be in addition to, or combined with step #7.

Step 9. Calculate desired parameters and derived parameters required for the CBC.

Step 10. Display all CBC parameters to an operator in a Graphical User Interface (GUI).

Step 11. Display results of WBC differential to an operator in the GUI.

Step 12. Display images of RBCs, WBCs, platelets and any unusual/abnormal blood elements to an operator.

Step 13. Allow an operator to interact with the images and the parameters to "sign off" the CBC, WBC differential count, and identification of unusual or abnormal objects.

Step 14. If needed, update results of CBC and WBC counts depending on operator interaction in step #13.

Step 15. Optionally, allow objects of interest to be relocated on a microscope that has a motorized, computer controllable stage to allow automated relocation of the objects for viewing.

Step 16. Optionally, update the results of the CBC and WBC counts depending on the microscopic operator interaction.

It is claimed:

1. A system for applying cells from a blood sample onto a substrate, comprising:
   a. an applicator tip for dispensing a fluid comprising blood onto a substrate; wherein the tip is arranged above the substrate;
   b. a computer containing a microprocessor;
   c. software instructions stored on a storage device for controlling the system, wherein when the microprocessor executes the software instructions the computer causes the system to:
      i. fill the applicator tip with a volume of the fluid;
      ii. position the applicator tip less than about 110 microns above the substrate; and
      iii. dispense a known volume of fluid out of the applicator tip and while the ejection of the fluid onto the substrate is occurring, maintaining relative movement between the tip and the substrate at a speed of about 10 to 100 mm per second to lay down the entire known volume of fluid in two or more rows over a defined area of the substrate such that cells in the fluid settle onto the substrate in a layer that is about one cell thick, wherein morphology of the cells is preserved sufficiently to enable image-based cell analysis; and
   d. a light receiving device for capturing an image of the cells on the substrate, wherein the computer causes the system to:
      i. capture an image of one of the rows of the fluid;
      ii. analyze the image to determine a width of the row of the fluid; and
      iii. change the position of the applicator tip relative to the substrate in the X or Y direction a distance equal to the width of the row of fluid.

2. The system of claim 1, wherein the computer causes the system to image the blood cells on the substrate and determine one or more of a red blood cell count, white blood cell count, and a platelet count.

3. The system of claim 1, wherein the computer causes the system to image the blood cells on the substrate and determine one or both of a complete blood count (CBC) and a white blood cell (WBC) differential.

4. The system of claim 1, wherein the computer controls movement of the tip relative to the substrate by instructing the system to change the position of the tip.

5. The system of claim 1, wherein the system further comprises a substrate controller and wherein the computer controls movement of the tip relative to the substrate by instructing the substrate controller to change the position of the substrate.

6. The system of claim 1, wherein the system further comprises a first reservoir for storing the blood, a second reservoir for storing a diluent, and a mixer for mixing the blood with the diluent to form a diluted fluid.

7. The system of claim 1, wherein the substrate comprises a slide and the computer causes the system to:
   a. apply a third row of fluid across the slide in a path having a fixed X or Y component, said third row comprising a layer of cells about one cell thick and a row width; and
   b. apply a fourth row of fluid across the slide along a path having a fixed X or Y component, said fourth row comprising a layer of cells about one cell thick and a row width;
   wherein the third row of fluid settles adjacent to the second row of fluid and the fourth row of fluid settles adjacent to the third row of fluid on the slide.

8. The system of claim 1, wherein the substrate comprises a slide and the system further comprises: a discharge unit for cleaning the slide; a dispenser for dispensing stain onto the slide; a slide tilter for tipping the slide to remove excess stain; a light receiving device for taking an image of the cells on the slide; a slide mover for positioning the slide under the light receiving device; and a light emission device for directing light onto or through the slide.

9. The system of claim 1, wherein the substrate comprises a slide and the system further comprises:
   a. a feeder for storing new slides;
   b. a first station where the applicator applies the rows of fluid onto the slide;
   c. a second station for staining, fixing, and drying the slides,
   d. a third station for illuminating and imaging the slides;
   e. a collector for receiving processed slides; and
   f. an advancer for moving the slides through the system starting from the feeder, moving the slides to a first station, the second station, the third station; and then the collector.

10. The system of claim 1, wherein the system further comprises a light source, and wherein the computer causes:
   a. the light source to:
      i. emit white light for illuminating the substrate;
      ii. apply a first light filter to the light to restrict the emission of the light to a first wavelength range; and
      iii. apply a second light filter to the light to restrict the emission of the light to a second wavelength range; and
   b. the light receiving device to capture one or more images of the cells on the substrate.

11. The system of claim 10, wherein the computer causes the light source to apply a third light filter to the light to restrict the emission of the light to a third wavelength range.

12. The system of claim 10, wherein the first wavelength range is 400 nm to 470 nm and the second wavelength range is 470 nm to 750 nm.

13. The system of claim 11, wherein specific wavelengths within the first, second, and third wavelength ranges are selected to be 430 nm, 500 nm, and 525 nm, or 600 nm, respectively.

14. The system of claim 10, wherein the computer causes the system to:
   a. refine the images by sharpening or compensating for spatial shifts or other distortions; and
   b. combine two or more images captured by the light receiving device when at least two separate wavelengths of light were directed at the slide to generate multicolor images for a display.

15. The system of claim 10, wherein the computer causes the system to determine spatial, densitometric, colorimetric, and texture features of the cells for classification of a cell type.

16. The system of claim 10, wherein the computer causes the system to:
   a. instruct the light receiving device to capture a black and white image of the substrate;
   b. correct focus and image quality by adjusting a focal distance of the lens; and
   c. shift a focal position of the lens while a number of filters are interposed between the slide and a light source.

17. The system of claim 10, wherein the light source comprises a halogen bulb for generating the white light, and a rotational motor for changing the positions of the filters.

18. The system of claim 1, wherein the system further comprises a light source, and wherein the computer causes:
   a. the light source to emit light within a first wavelength range with a first light emitting diode (LED);
   b. the light source to emit light within a second wavelength range with a second LED;
   c. the light receiving device to capture one or more images of the cells on the substrate; and
   d. the system to shift a focal position of light emanating from at least one of the LEDs.

19. The system of claim 1, wherein the rows are non-touching rows.

20. The system of claim 1, wherein the two or more rows are formed by the applicator tip dispensing the fluid in a first row in a first direction and then turning and moving in a second direction opposite the first direction and in parallel to the first row to lay down a second row adjacent the first row.

21. The system of claim 1, wherein the two or more rows are laid down on the substrate in a spiral pattern.

22. The system of claim 1, wherein the two or more rows are laid down on the substrate and settle adjacent one another to form a gapless or contiguous flow of cells in the defined area.

23. The system of claim 1, wherein the system further comprises a light source arranged to separately emit a first light in a wavelength range of 400 to 470 nm and a second light in a wavelength range of 470 to 750 nm onto the rows of fluid on the substrate.

24. The system of claim 23, wherein the first light has a wavelength of 430 nm and the second light has a wavelength of 600 nm.

25. The system of claim 1, wherein the computer causes the system to direct fluid out of the applicator tip at a flow rate of about 0.1 microliters per second.

26. The system of claim 1, wherein the computer causes the system to maintain relative movement between the applicator tip and the substrate at a speed of about 30 mm per second.

27. The system of claim 18, wherein the first wavelength range is 400 nm to 470 nm and the second wavelength range is 470 to 750 nm.

28. The system of claim 18, wherein the computer causes the light source to emit light within a third wavelength range with a third LED.

29. The system of claim 28, wherein wavelengths within the first, second, and third wavelength ranges are 430 nm, 500 nm, and 525 nm or 600 nm, respectively.

30. A system for analyzing cells from a blood sample, comprising:
   a. an applicator tip for dispensing a fluid comprising blood onto a substrate; wherein the tip is arranged above the substrate;
   b. a light source configured to emit onto cells on the substrate light in a first wavelength range of 400 to 470 nm and light in a second wavelength range of 470 to 750 nm;
   c. a light receiving device arranged to capture one or more black and white images of the cells on the substrate;
   d. a computer containing a microprocessor; and
   e. software instructions stored on a storage device for controlling the system, wherein when the microprocessor executes the software instructions the computer causes the system to:
      i. fill the applicator tip with a volume of the fluid;
      ii. position the applicator tip less than about 110 microns above the substrate;
      iii. dispense a known volume of fluid out of the applicator tip and while ejection of the fluid onto the substrate is occurring, maintaining relative movement between the tip and the substrate to lay down the entire known volume of fluid in two or more rows over a defined area of the substrate; wherein the applicator tip height above the substrate, a flow rate of the fluid out of the applicator tip, and a speed of the relative movement are selected such that cells in the fluid settle onto the substrate in a layer that is about one cell thick, and such that morphology of the cells is sufficiently preserved to enable image-based cell analysis;
iv. control the light source to emit light onto the cells on the substrate at the first wavelength range;
v. activate the light receiving device to capture a black and white image of the cells on the substrate at the first wavelength range;
vi. control the light source to emit light onto the cells on the substrate at the second wavelength range;
vii. activate the light receiving device to capture a black and white image of the cells on the substrate at the second wavelength range;
viii. analyze the black and white images of the cells from the blood sample;
ix. capture an image of one of the rows of the fluid;
x. analyze the image to determine a width of the row of the fluid; and
xi. change the position of the applicator tip relative to the substrate in the X or Y direction a distance equal to the width of the row of fluid.

* * * * *

UNITED STATES PATENT AND TRADEMARK OFFICE
CERTIFICATE OF CORRECTION

PATENT NO. : 9,017,610 B2  
APPLICATION NO. : 12/430885  
DATED : April 28, 2015  
INVENTOR(S) : James Winkelman, Milenko Tanasijevic and David Zahniser It is certified that error appears in the above-identified patent and that said Letters Patent is hereby corrected as shown below:

In the claims

In Claim 8, column 20-21, line 67 (column 20) and line 1 (column 21), after "stain;" delete "a light receiving device for taking an image of the cells on the slide;".

Signed and Sealed this  
Twentieth Day of October, 2015

Michelle K. Lee  
*Director of the United States Patent and Trademark Office*